United States Patent
Carpenter et al.

(10) Patent No.: US 9,594,052 B2
(45) Date of Patent: Mar. 14, 2017

(54) METHODS OF FAILSAFING ELECTROCHEMICAL MEASUREMENTS OF AN ANALYTE AS WELL AS DEVICES, APPARATUSES AND SYSTEMS INCORPORATING THE SAME

(71) Applicant: Roche Diabetes Care, Inc., Indianapolis, IN (US)

(72) Inventors: Scott E. Carpenter, Pendleton, IN (US); Siva Chittajallu, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 14/851,807

(22) Filed: Sep. 11, 2015

(65) Prior Publication Data

US 2015/0377828 A1 Dec. 31, 2015

Related U.S. Application Data

(63) Continuation of application No. PCT/EP2014/054955, filed on Mar. 13, 2014.

(Continued)

(51) Int. Cl.
*G01N 27/327* (2006.01)
*G01N 27/416* (2006.01)

(52) U.S. Cl.
CPC ..... *G01N 27/4163* (2013.01); *G01N 27/3274* (2013.01)

(58) Field of Classification Search
CPC .............. G01N 27/327–27/3274; G01N 27/48
See application file for complete search history.

(56) References Cited

U.S. PATENT DOCUMENTS

2003/0060692 A1 3/2003 Ruchti et al.
2003/0104119 A1* 6/2003 Wilson .................. C12Q 1/001
427/2.1

(Continued)

FOREIGN PATENT DOCUMENTS

EP 1156324 A1 11/2001
EP 2042865 A2 4/2009

(Continued)

OTHER PUBLICATIONS

Mugweru et al. "Redox Protein-Polymer Films for Simultaneous Determination of Ascorbic Acid and Hydrogen Peroxide", Analytical Sciences Sep. 2008 vol. 24 pp. 1105-1110.*

(Continued)

*Primary Examiner* — Alexander Noguerola

(57) ABSTRACT

Methods are disclosed for measuring an analyte concentration in a fluidic sample. Such methods further allow one to provide an error code or correct and/or compensate for interferents such as an antioxidant before providing an analyte concentration. The measurement methods utilize information obtained from test sequences having at least one DC block, where DC block includes at least one recovery potential, and where a closed circuit condition of the electrode system is maintained during the DC block. The methods use information relating to status of a redox mediator during the electrochemical analysis to provide a statistical antioxidant failsafe using either a classifier or a discriminator to determine whether the antioxidant is interfering with the analyte concentration. Also disclosed are devices, apparatuses and systems incorporating the various measurement methods.

9 Claims, 11 Drawing Sheets

Related U.S. Application Data

(60) Provisional application No. 61/793,377, filed on Mar. 15, 2013.

(56) References Cited

U.S. PATENT DOCUMENTS

| | | |
|---|---|---|
| 2004/0157339 A1 | 8/2004 | Burke et al. |
| 2005/0279631 A1 | 12/2005 | Celentano |
| 2007/0102292 A1 | 5/2007 | Dreibholz et al. |
| 2009/0030641 A1 | 1/2009 | Fjield et al. |
| 2009/0084687 A1* | 4/2009 | Chatelier ............... C12Q 1/001 205/792 |
| 2011/0139617 A1* | 6/2011 | Fransaer ................ C07K 17/00 204/403.14 |

FOREIGN PATENT DOCUMENTS

| | | |
|---|---|---|
| EP | 2138841 A2 | 12/2009 |
| EP | 2261646 B1 | 7/2015 |
| WO | 9932881 A1 | 7/1999 |
| WO | 0121827 A1 | 3/2001 |
| WO | 03060154 A2 | 7/2003 |
| WO | 2006109279 A2 | 10/2006 |
| WO | 2007100651 A1 | 9/2007 |
| WO | 2008036516 A1 | 3/2008 |
| WO | 2009075951 A1 | 6/2009 |
| WO | 2012134890 A1 | 10/2012 |

OTHER PUBLICATIONS

Blood Glucose Monitoring: The Facts about Accuracy published by Roche Accu-Chek®, 2011, sixteen pages.*

Gunasingham; et al., "Pulsed amperometric detection of glucose using a mediated enzyme electrode", Journal of Electroanalytical Chemistry and Interfacial Electrochemistry, Jul. 25, 1990, vol. 287, No. 2, pp. 349-362.

* cited by examiner

METHODS OF FAILSAFING ELECTROCHEMICAL MEASUREMENTS OF AN ANALYTE AS WELL AS DEVICES, APPARATUSES AND SYSTEMS INCORPORATING THE SAME

CROSS-REFERENCE TO RELATED APPLICATIONS

This patent application is a continuation of Intl Patent Application No. PCT/EP2014/054955 (filed 13 Mar. 2014), which claims priority to and the benefit of U.S. Provisional Patent Application No. 61/793,377 (filed 15 Mar. 2013). Each patent application is incorporated herein by reference as if set forth in its entirety.

TECHNICAL FIELD

The disclosure relates generally to mathematics and medicine, and more particularly, it relates to methods of electrochemically measuring an analyte in a fluidic sample and providing an antioxidant failsafe and/or a reagent health failsafe that prevents erroneously reporting of a falsely elevated analyte concentration due to the antioxidant interference and/or reagent failures, and even correcting the analyte concentration.

BACKGROUND

Significant benefits can be realized from electrochemically measuring analytes in fluidic samples (i.e., biological or environmental). For example, diabetic treatment with self-monitoring blood glucose (SMBG) devices and systems contributes to improving glycemic control and attenuating diabetes-related morbidity. Therefore, the accuracy of SMBG devices and systems is important for optimal glycemic control.

The accuracy, however, of present methods of electrochemically measuring analytes such as glucose can be negatively affected by a number of interferents including antioxidants or other reducing agents. Because of their benefits, there is an increasing number of medical uses, as well as off-label therapies and alternative medicine procedures, in which megadoses of antioxidants are administered by injection or intravenously. For example, burn patents often are treated with parenteral doses of ascorbate, resulting in blood plasma levels of 40 mg/dL or more. There also are alternative cancer therapies that prescribe much larger doses, resulting in ascorbate levels as high as 400 mg/dL. Unfortunately, high doses of antioxidants such as ascorbate can interfere with the electrochemical response of SMGB devices and systems and can cause them to report falsely elevated glucose concentrations, which presents a significant disadvantage for an individual with diabetes receiving an antioxidant therapy. Specifically, if an individual is in a euglycemic state, but responds to the falsely elevated glucose concentration by administering insulin, this could result in hypoglycemia and/or death. The Food and Drug Administration suggests that ascorbate interference exists for some electrochemical assays even at 3 mg/dL of ascorbate.

Current electrochemical SMBG methods, devices and systems provide individuals having diabetes advantages with respect to convenience; however, there remains a need for improved methods of electrochemically measuring an analyte in a fluid sample with additional quality checks for the presence of interferents such as an antioxidant or for detecting a failure with the biosensor reagent system.

BRIEF SUMMARY

In view of the disadvantages noted above, the disclosure describes methods of detecting an interferent and in some instances failsafing an electrochemical measurement of an analyte that may be biased. The methods are based upon an inventive concept that includes using information derived from a test sequence that provides alternating current (AC) and/or direct current (DC) responses, which can be designed to provide specific information about an impact of an interferent such as an antioxidant that is present in the fluidic sample on a redox mediator of an electrochemical analyte measurement system. For example, information such as current response, shape and/or magnitude of an excitation pulse and/or a recovery pulse from a DC block can be used to failsafe against falsely elevated results due to antioxidant interference. In particular, the methods use information relating to a redox mediator derived from at least one DC block to discriminate between antioxidant levels at which the analyte prediction bias of an electrochemical system is acceptable and antioxidant levels at which the analyte prediction bias is clinically unacceptable. The methods therefore aid in ensuring patient safety. Specifically, it has been found that antioxidants can increase an amount of a reduced form of some redox mediators, thereby falsely increasing current detected during the electrochemical analysis. Moreover, it has been found that information pertaining to status of the redox mediator during an electrochemical analysis can be used to detect a reagent layer failure. The inventive concept therefore provides certain advantages, effects, features and objects when compared to known methods of measuring an analyte concentration (or value) in a fluidic sample and thereby attenuate incidents of erroneously reporting falsely elevated analyte concentration due to antioxidants and/or reagent failures.

In one aspect, an electrochemical analysis method is provided for measuring, determining, calculating or otherwise predicting an analyte concentration in a fluidic sample having an antioxidant, where the method includes an antioxidant failsafe. The method can include the steps of providing a test sequence of at least one DC block to the fluidic sample and measuring the response information thereto, where the at least one DC block is designed to elicit specific information about different aspects of the sample and/or the biosensor, including a redox mediator status.

In some instances, the test sequence also can include at least one AC block. In other instances, the test sequence also can include a second DC block. In still other instances, the test sequence includes the at least one AC block, the at least one DC block and the second DC block.

The at least one DC block is a continuous, pulsed excitation waveform (i.e., the potential is applied and controlled throughout the DC block in a closed circuit), which is in contrast to some pulsed amperometric methods that employ an open circuit between excitation pulses. The DC block includes a plurality of short-duration excitation pulses and recovery pulses optimized for detecting an analyte such as glucose, the optimization pertaining to pulse duration, ramped transitions between the excitation pulse and recovery pulse, number of current responses measured during each pulse, and where in each pulse current response measurements are taken. The DC block can be from at least one (1) pulse to about ten (10) pulses at a potential that alternates between about 0 mV to about +450 mV in a closed circuit.

Each pulse can be applied for about 50 msec to about 500 msec. Moreover, the ramp rate can be from about 10 mV/msec to about 50 mV/msec.

Alternatively, the at least one DC block is a slow-ramped bi-polar potential (SRBP) waveform with intervals that alternate or cycle between potentials of about −450 mV to about +450 mV in a closed circuit. Each interval can be applied for about 100 msec to about 5 sec. Moreover, the ramp rate can be from about 0.500 mV/msec to ≤about 45 mV/msec.

When included, the AC block can be a plurality of low-amplitude AC signals.

In addition, the method can include a step of providing a statistical antioxidant failsafe using either a classifier or a discriminator that distinguishes between samples containing antioxidant levels with less than a predetermined concentration from samples that have antioxidant levels that are greater than the predetermined concentration, where the failsafe is based upon information from the at least one DC block relating to status of a redox mediator during the electrochemical analysis.

In some instances, the information relating to status of the redox mediator is an amount of an oxidized form of the redox mediator ($M_{ox}$) and/or an amount of a reduced form of the redox mediator ($M_{red}$).

In some instances, the antioxidant is ascorbate, the analyte is glucose, and the redox mediator is a nitrosoanaline (NA)-derived redox mediator, where the $M_{ox}$ and the $M_{red}$ are quinonediimine (QDI) and phenylenediamine (PDA), respectively. As such, a current response to a DC block having a plurality of pulses would correspond primarily to the amount of PDA, which is proportional to the amount of glucose present. In contrast, a current response to a DC block having a plurality of SRBPs would provide quantitative information about the levels of QDI, as well as PDA.

In another aspect, an electrochemical analysis method is provided for measuring, determining, calculating or otherwise predicting an analyte concentration in a fluidic sample, where the method includes a reagent layer health failsafe. The method, as above, can include a step of providing a test sequence of at least one DC block to the fluidic sample as described above and measuring response information thereto. The reagent layer health failsafe, however, includes checking for a simple existence or absence of a $M_{ox}$ feature or a $M_{red}$ feature as a basis for the reagent layer health failsafe.

In either aspect above, where the measurement indicates a potential for a clinically significant bias, the analyte concentration is not displayed and instead is failsafed (i.e., not reported) with an appropriate message of suspected interference, reagent layer failure or even a general biosensor failure.

In view of the foregoing, devices, apparatuses and systems used in connection with electrochemical analysis are provided that incorporate one or more of the measurement methods disclosed herein. These devices, apparatuses and systems can be used to determine concentration of analytes including, but not limited to, amino acids, antibodies, bacteria, carbohydrates, drugs, lipids, markers, nucleic acids, peptides, proteins, toxins, viruses and other analytes, as well as combinations thereof, in the presence of an antioxidant. In some instances, the antioxidant is ascorbate, and the analyte is glucose.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Figure 1:
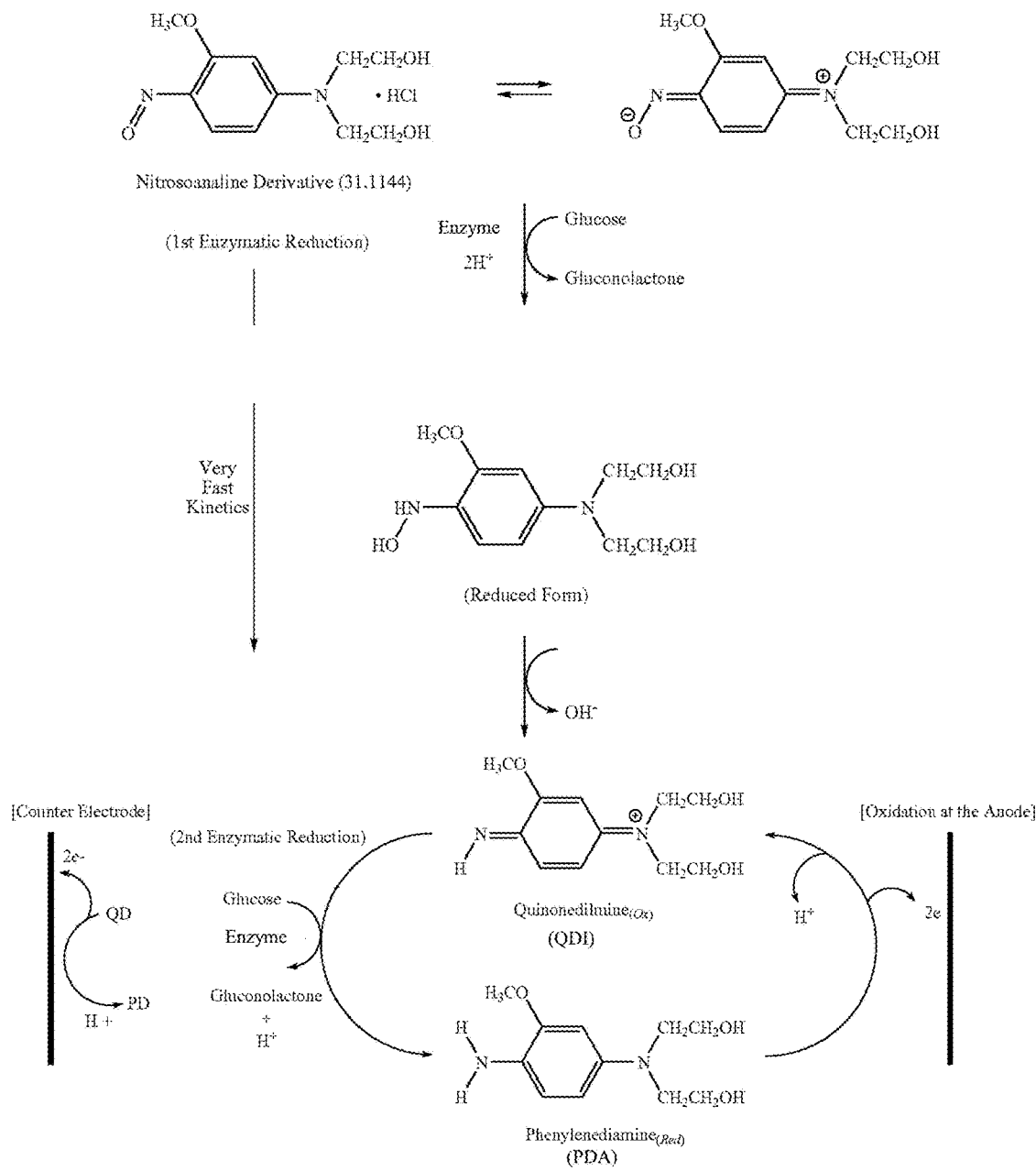
FIG. 1 shows an exemplary electrochemical reaction and its electron transfer pathway from a NA-derived redox mediator to a working electrode of an exemplary analyte measurement system.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The methods, devices, apparatuses and systems now will be described more fully hereinafter with reference to the accompanying drawings, in which some, but not all embodiments of the inventive concept are shown. Indeed, the inventive concept may be embodied in many different forms and should not be construed as limited to the embodiments set forth herein; rather, these embodiments are provided so that this disclosure will satisfy applicable legal requirements.

Likewise, many modifications and other embodiments of the methods, devices, apparatuses and systems described herein will come to mind to one of skill in the art to which the disclosure pertains having the benefit of the teachings presented in the foregoing descriptions and the associated drawings. Therefore, it is to be understood that the inventive concept is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the present methods, devices, apparatuses and systems, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

Overview

Analyte measurement methods are disclosed herein that use information derived from AC and/or DC current responses to provide an analyte concentration in a reliable manner. In particular, the methods use information relating to status of a redox mediator obtained from at least one block of DC pulses to discriminate between antioxidant levels at which the analyte prediction bias of an electrochemical system is acceptable and antioxidant levels at which the analyte prediction bias is clinically unacceptable is essential to ensure patient safety. The measuring methods therefore can be used to reduce the effects of interferents such as an antioxidant on an analyte concentration measurement, thereby providing a more "true" analyte concentration or even preventing a reporting of a falsely elevated analyte concentration.

In the examples below, a NA-derived redox mediator was used. However, based upon the general teachings herein, one of skill in the art will understand how to select appropriate potential differences for the applied potentials for regions of excitation of diffusion-limited current and regions of recovery or current that is not diffusion-limited based upon a selected redox mediator. Here, the selection of about +450 mV and about 0 mV is appropriate for excitation and recovery pulses with NA-derived redox mediators. It is understood that even for such NA-derived redox mediators, there are acceptable ranges of greater applied potential for diffusion-limited current and similarly and there are acceptable ranges for the applied recovery potential. Each redox mediator therefore will have a specific redox potential and characteristic electron transfer kinetics from which one of skill in the art could select the appropriate potential differences for excitation or recovery.

As used herein, "nitrosoaniline-derived redox mediator" or "NA-derived redox mediator" means a substituted nitrosoanline compound as described in, for example, U.S. Pat. No. 5,122,244. An example of a NA-derived redox mediator is N,N-bis(hydroxyethyl)-3-methoxy-4-nitrosoaniline hydrochloride. Other examples of NA-derived redox mediators include, but are not limited to, 4,6-dinitro-2-nitrosoaniline, N'-bis-(2-hydroxyethyl)-p-nitrosoaniline, N,N'-dimethyl-p-nitrosoaniline, N,N'-diethyl-p-nitrosoaniline, N-methyl-N'-(4-nitrosophenyl)-piperazine, N-(2-hydroxyethyl)-5-nitrosoindoline, 2,4-dimethoxy-nitrosobenzene, N,N'-bis-(2-methoxyethyl)-4-nitrosoaniline, N-(4-nitrosophenyl)-morpholine, N-(2,2-diethoxy-ethyl)N'-(4-nitrosophenyl)-piperazine, p-nitrosophenol, 3-methoxy-4-nitrosophenol, N-(2-hydroxyethyl)-N'-p-nitrosophenyl-piperazine, N,N-bis-(2-hydroxyethyl)-p-nitrosoaniline, o-methoxy-N,N-bis-(2-hydroxyethyl)]-p-nitrosoaniline, p-hydroxynitrosobenzene, N-methyl-N'-(4-nitrosophenyl)-piperazine, p-quinone dioxime, N,N-dimethyl-p-nitrosoaniline, N,N-diethyl-p-nitrosoaniline, N-(4-nitrosophenyl)-morpholine, N-benzyl-N-(5'-carboxypentyl)-p-nitrosoaniline, N,N-dimethyl-4-nitroso-1-naphthylamine, N,N,3-trimethyl-4-nitrosoaniline, N-(2-hydroxyethyl)-5-nitrosoindoline, N,N-bis-(2-hydroxyethyl)-3-chloro-4-nitrosoaniline, 2,4-dimethoxy-nitrosobenzene, N,N-bis-(2-methoxyethyl)-4-nitrosoaniline, 3-methoxy-4-nitrosophenol, N-(2-hydroxyethyl)-6-nitroso-1,2,3 tetrahydroquinoline, N,N-dimethyl-3-chloro-4-nitrosoaniline, N,N-bis-(2-hydroxyethyl)-3-fluoro-4-nitrosoaniline, N,N-bis-(2-hydroxyethyl)-3-methylthio-4-nitrosoaniline, N-(2-hydroxyethyl)-N-(2-(2-methoxyethoxy)-ethyl)-4-nitrosoaniline, N-(2-hydroxyethyl)-N-(3-methoxy-2-hydroxy-1-propyl)-4-nitrosoaniline, N-(2-hydroxyethyl)-N-(3-(2-hydroxyethoxy)-2-hydroxy-1-propyl)-4-nitrosoaniline, N-(2-hydroxyethyl)-N-(2-(2-hydroxyethoxy)-ethyl)-4-nitrosoanaline, 3-(4'-chloro-phenylimino)-3H-phenothiazine, 3-(4'-diethylamino-phenylimino)-3H-phenothiazine, 3-(4'-ethyl-phenylimino)-3H-phenothiazine, 3-(4'-trifluoromethyl-phenylimino)-3H-phenothiazine, 3-(4'-methoxycarbonyl-phenylimino)-3H-phenothiazine, 3-(4'-nitro-phenylimino)-3H-phenothiazine, 3-(4'-methoxy-phenylimino)-3H-phenothiazine, 7-acetyl-3-(4'-methoxycarbonylphenylimino)-3H-phenothiazine, 7-trifluoromethyl-3-(4'-methoxycarbonylphenylimino)-3H-phenothiazine, 3-(4'-omega-carboxy-n-butyl-phenylimino)-3H-phenothiazine, 3-(4'-aminomethyl-phenylimino)-3H-phenothiazine, 3-(4'-(2"-(5"-(p-aminophenyl)-1,3,4-oxadiazoyl)phenylimino)-3H-phenothiazine, 3-(4'-β-aminoethyl-phenylimino)-3H-phenothiazine, 6-(4'-ethylphenyl)amino-3-(4'-ethyl-phenylimino)-3H-phenothiazine, 6-(4'-[2-(2-ethanoloxyl)ethoxy]ethoxyphenyl)amino-3-(4'-[2-(2-ethanoloxyl)ethoxy]ethoxy-phenylimino-3H-phenothiazine, 3-(4'-[2-(2-ethanoloxyl)ethoxy]ethoxy-phenylimino-3H-phenothiazine, 3-(4'-phenylimino)-3H-phenothiazineboronic acid, (3-(3',5'-dicarboxy-phenylimino)-3H-phenothiazine, 3-(4'-carboxy-phenylimino)-3H-phenothiazine, 3-(3',5'-dicarboxy-phenylimino)-3H-phenoxazine, 3-(3',5'-phenylimino)-3H-phenothiazinedisulfonic acid, 3-(3-phenylimino)-3H-phenothiazinesulfonic acid, and combinations thereof. See also, U.S. Pat. Nos. 5,122,244 and 5,286,362.

As used herein, "antioxidant" or "antioxidants" means a compound or substance that can prevent damage caused by unstable molecules, such as free radicals and active oxygen species (i.e., prevents damage caused by oxidation from singlet oxygen, hydrogen peroxide, hydroxyl radical, etc.). As reducing agents, antioxidants may exert their effects in two ways: (1) as direct-acting antioxidants that inactivate oxidative agents such as free radicals; and (2) as indirect agents that can modulate the function, activity or level of other antioxidants or antioxidant mechanisms. Of interest herein are antioxidants that reduce a redox mediator in an electrochemical enzymatic analyte measurement system. Examples of antioxidants typically used in a clinical setting include, but are not limited to, ascorbate (also known as Vitamin C or ascorbic acid), citric acid, deferoxamine (DFO), glutathione, N-acetylcysteine (NAC), pyrrolidine dithiocarbamate (PDTC), trylizad-mesylate (TLM) and uric acid.

FIG. 1 shows an exemplary electrochemical reaction and electron transfer pathway from a NA-derived redox mediator to the working electrode of an exemplary analyte measurement system. The electrochemical reaction in FIG. 1 may occur in an electrochemical biosensor 20 in response to an analyte such as glucose, where NA forms an intermediate that quickly converts to QDI and then is reduced to PDA. Each molecule of PDA can be oxidized at the working electrode to liberate two electrons, which are detected by the working electrode, also resulting in the cyclical re-formation of QDI. Ascorbate, being an effective reducing agent, reacts rapidly with QDI, thereby increasing the amount of PDA, resulting in a higher current being detected at the working electrode. It is this perceived higher current that is then translated into a falsely-elevated blood glucose (bG) concentration. One of skill in the art will appreciate that a similar effect may be caused by any potential interferent that is an effective reducing agent reacting rapidly with QDI to produce excess PDA in this manner. Generally stated, a falsely-elevated bG concentration may result from any interferent that is effective at rapidly converting $M_{ox}$ to produce an artificially high amount of the corresponding $M_{red}$.

More specifically, and as shown in FIG. 1, the NA-derived redox mediator reacts with a reduced form of an enzyme (e.g., flavin adenine dinucleotide-dependent glucose dehydrogenase (FAD-GDH) or pyrroloquinoline quinone glucose dehydrogenase (PQQ-GDH)) that catalyzes the oxidation of glucose in the presence of an electron acceptor to produce a reduced NA-derived redox mediator that quickly undergoes hydrolysis to form QDI. QDI then reacts through a second enzymatic reduction to form PDA. As above, each molecule of PDA can be oxidized to liberate two electrons, which are detected by the working electrode, also resulting in the cyclical re-formation of QDI. Ascorbate, however, causes a perceived higher current by increasing the amount of PDA, which is then translated into a falsely-elevated bG concentration.

It shall be understood, however, that while certain exemplary embodiments deal with biosensors that use NA as the redox mediator, other reagent layer chemistries and redox mediators can utilize the same inventive concept such as the one described herein. It therefore shall further be appreciated that the electrochemical reaction of FIG. 1 and the use of a NA-derived redox mediator are non-limiting examples, and that the methods, devices, apparatuses and systems disclosed herein may be used in connection with a plurality of enzymes and different redox mediators.

Advantageously, the measurement methods provide an ability to discriminate between antioxidant levels at which the analyte prediction bias of an electrochemical system is acceptable and antioxidant levels at which the antioxidant prediction bias is clinically unacceptable to ensure patient safety. Such methods may provide this functionality without the need for information that is different from that which is used for analyte prediction (e.g., glucose prediction). In some instances, an approach is used for discriminating antioxidant levels that result in a biased analyte estimate that is either acceptable or unacceptable from a clinical perspective. Other instances implement this capability in the form of an antioxidant failsafe within the SMBG meter. If the failsafe is triggered, a meter can be configured to deliver an error code or a specific antioxidant interference error message rather than an inaccurate analyte concentration.

For example, the failsafe could include direct messaging such as: "An antioxidant level was detected to be greater than the acceptable range for this blood glucose assay and thus a glucose value cannot be reported." This could result in a health care professional follow up to determine the cause and find a suitable clinical analyzer that may not have a bias due to this antioxidant.

Other instances include a "reagent layer health" or "chemistry health" failsafe for determining whether the reagent layer and redox mediator of the biosensor are working properly, or whether the reagent layer is compromised by any number of different interferents. As such, the failsafe could include direct messaging such as: "A reagent layer health error was detected on the biosensor and thus a glucose value cannot be reported" or "A chemistry health error was detected on the biosensor and thus a glucose value cannot be reported." This could result in a user selecting a new biosensor to repeat the electrochemical measurement.

As used herein, "reagent layer health" or "chemistry health" means an ability of a test system reagent, mediator and/or mediator precursor in contact with a test sample to provide a desired electrochemical response to an applied test signal which is not unacceptably impacted or impaired by any of a plurality of interferents either known or unknown.

The measurement methods disclosed herein largely utilize amperometry; however, it is contemplated that the methods can be used with other electrochemical measurement methods (e.g., coulometry, potentiometry or voltammetry). Additional details regarding exemplary electrochemical measurement methods are disclosed in, for example, U.S. Pat. Nos. 4,008,448; 4,225,410; 4,233,029; 4,323,536; 4,891,319; 4,919,770; 4,963,814; 4,999,582; 4,999,632; 5,053,199; 5,108,564; 5,120,420; 5,122,244; 5,128,015; 5,243,516; 5,288,636; 5,352,351; 5,366,609; 5,385,846; 5,405,511; 5,413,690; 5,437,999; 5,438,271; 5,508,171; 5,526,111; 5,627,075; 5,628,890; 5,682,884; 5,727,548; 5,762,770; 5,858,691; 5,997,817; 6,004,441; 6,054,039; 6,254,736; 6,270,637; 6,645,368; 6,662,439; 7,073,246; 7,018,843; 7,018,848; 7,045,054; 7,115,362; 7,276,146; 7,276,147; 7,335,286; 7,338,639; 7,386,937; 7,390,667; 7,407,811; 7,429,865; 7,452,457; 7,488,601; 7,494,816; 7,545,148; 7,556,723; 7,569,126; 7,597,793; 7,638,033; 7,731,835; 7,751,864; 7,977,112; 7,981,363; 8,148,164; 8,298,828; 8,329,026; 8,377,707; and 8,420,404, as well as RE36268, RE42560, RE42924 and RE42953.

Advantageously, the methods described herein can be incorporated into SMBG devices, apparatuses and systems to more accurately and quickly report an analyte concentration, such as a glucose concentration, especially a blood glucose concentration.

Moreover, the measurement methods can be implemented using advanced microprocessor-based algorithms and processes that result in dramatically improved system performance. These measurement methods also offer flexibility and number of ways to create algorithms that can achieve improved performance such as 10/10 performance. As used herein, "10/10 performance" means that a measured bG value is within about ±10% of the actual bG value for bG concentrations >100 mg/dL, and within ±10 mg/dL of the actual bG value for bG concentrations <100 mg/dL.

Details regarding additional electrochemical measurement methods that may be useful in performing the methods disclosed herein can be found in the following co-filed and co-pending patent applications titled: "METHODS OF SCALING DATA USED TO CONSTRUCT BIOSENSOR ALGORITHMS AS WELL AS DEVICES, APPARATUSES AND SYSTEMS INCORPORATING THE SAME" (Intl Patent Application No. PCT/EP2014/054952); "METHODS OF ELECTROCHEMICALLY MEASURING AN ANALYTE WITH A TEST SEQUENCE HAVING A PULSED DC BLOCK AS WELL AS DEVICES, APPARATUSES AND SYSTEMS INCORPORATING THE SAME" (Intl Patent Application No. PCT/EP2014/054965); "METHODS OF USING INFORMATION FROM RECOVERY PULSES IN ELECTROCHEMICAL ANALYTE MEASUREMENTS AS WELL AS DEVICES, APPARATUSES AND SYSTEMS INCORPORATING THE SAME" (Intl Patent Application No. PCT/EP2014/054943); "DESCRIPTOR-BASED METHODS OF ELECTROCHEMICALLY MEASURING AN ANALYTE AS WELL AS DEVICES, APPARATUSES AND SYSTEMS INCORPORATING THE SAME" (Intl Patent Application No. PCT/EP2014/054956); and "METHODS OF DETECTING HIGH ANTIOXIDANT LEVELS DURING ELECTROCHEMICAL MEASUREMENTS AND FAILSAFING AN ANALYTE CONCENTRATION THEREFROM AS WELL AS DEVICES, APPARATUSES AND SYSTEMS INCORPORATING THE SAME" (Intl Patent Application No. PCT/EP2014/054962).

Analyte Measurement Devices, Apparatuses and Systems

Figure 2:
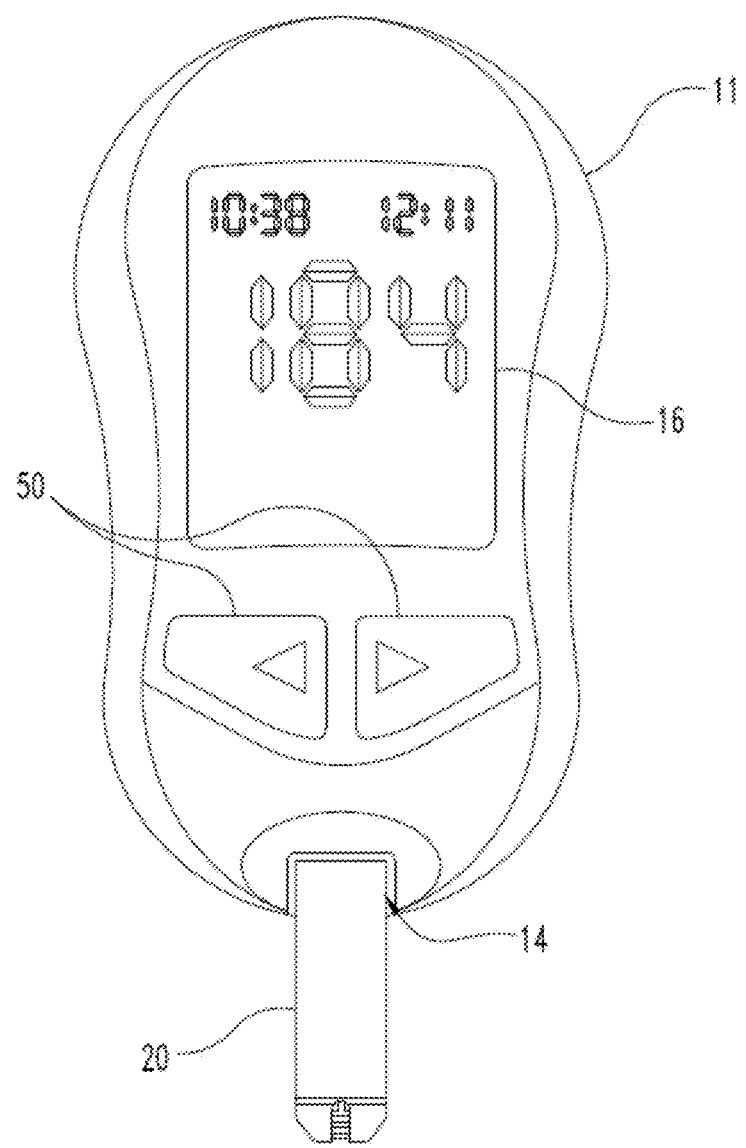
FIG. 2 shows an exemplary analyte measurement system including a meter and a biosensor.

Prior to, and in connection with, describing the inventive measurement methods, FIG. 2 shows an exemplary analyte measurement system including a device such as a test meter 11 operatively coupled with an electrochemical biosensor 20 (also known as a test element). Meter 11 and biosensor 20 are operable to determine concentration of one or more analytes in a fluidic sample provided to the biosensor 20. In some instances, the sample may be a body fluid sample such as, for example, whole blood, plasma, serum, urine or saliva. In other instances, the fluidic sample may be another type of sample to be tested for the presence or concentration of one or more electrochemically reactive analyte(s) such as an aqueous environmental sample.

In FIG. 2, the biosensor 20 is a single use test strip removably inserted into a connection terminal 14 of meter 11. In some instances, biosensor 20 is configured as a blood glucose test element and includes features and functionalities for electrochemically measuring glucose. In other instances, biosensor 20 is configured to electrochemically measure one or more other analytes such as, for example, amino acids, antibodies, bacteria, carbohydrates, drugs, lipids, markers, nucleic acids, peptides, proteins, toxins, viruses, and other analytes.

Meter 11 includes an electronic display 16 that is used to display various types of information to the user including analyte concentration(s) or other test results, and user interface 50 for receiving user input. Meter 11 further includes a microcontroller and associated test signal generating and measuring circuitry (not shown) that are operable to generate a test signal, to apply the signal to the biosensor 20, and to measure one or more responses of the biosensor 20 to the test signal. In some instances, meter 11 can be configured as a blood glucose measurement meter and includes features and functionalities of the ACCU-CHEK® AVIVA® meter as described in the booklet "Accu-Chek® Aviva Blood Glucose Meter Owner's Booklet" (2007), portions of which are disclosed in U.S. Pat. No. 6,645,368. In other instances, meter 11 can be configured to electrochemically measure one or more other analytes such as, for example, amino acids, antibodies, bacteria, carbohydrates, drugs, lipids, markers, nucleic acids, proteins, peptides, toxins, viruses, and other analytes. Additional details regarding exemplary meters configured for use with electrochemical measurement methods are disclosed in, for example, U.S. Pat. Nos. 4,720,372; 4,963,814; 4,999,582; 4,999,632; 5,243,516; 5,282,950; 5,366,609; 5,371,687; 5,379,214; 5,405,511; 5,438,271; 5,594,906; 6,134,504; 6,144,922; 6,413,213; 6,425,863; 6,635,167; 6,645,368; 6,787,109; 6,927,749; 6,945,955; 7,208,119; 7,291,107; 7,347,973; 7,569,126; 7,601,299; 7,638,095 and 8,431,408.

One of skill in the art understands that the measurement methods described herein can be used in other measurement, devices, apparatuses, systems and environments such as, for example, hospital test systems, laboratory test systems and others.

It shall be understood that the biosensor and meter can include additional and/or alternate attributes and features in addition to or instead of those shown in FIG. 2. For example, the biosensor can be in the form of a single use, disposable electrochemical test strip having a substantially rectangular shape. It shall be appreciated that the biosensors can include different forms such as, for example, test strips of different configurations, dimensions or shapes, non-strip test elements, disposable test elements, reusable test elements, micro-arrays, lab-on-chip devices, bio-chips, bio-discs, bio-cds or other test elements. In some instances, the biosensor can include additional electrodes and reagents such as, for example, a dual assay biosensor for detecting glucose and ketones. See, e.g., U.S. patent application Ser. Nos. 13/667,057 and 13/667,154. Additional details regarding exemplary biosensors configured for use with electrochemical measurement methods are disclosed in, for example, U.S. Pat. Nos. 5,694,932; 5,762,770; 5,948,695; 5,975,153; 5,997,817; 6,001,239; 6,025,203; 6,162,639; 6,245,215; 6,271,045; 6,319,719; 6,406,672; 6,413,395; 6,428,664; 6,447,657; 6,451,264; 6,455,324; 6,488,828; 6,506,575; 6,540,890; 6,562,210; 6,582,573; 6,592,815; 6,627,057; 6,638,772; 6,755,949; 6,767,440; 6,780,296; 6,780,651; 6,814,843; 6,814,844; 6,858,433; 6,866,758; 7,008,799; 7,063,774; 7,238,534; 7,473,398; 7,476,827; 7,479,211; 7,510,643; 7,727,467; 7,780,827; 7,820,451; 7,867,369; 7,892,849; 8,180,423; 8,298,401; 8,329,026, as well as RE42560, RE42924 and RE42953.

Measurement Methods

Measurement Methods Having an Antioxidant Failsafe: As noted above, the measurement methods described herein are based upon an inventive concept that includes using information derived from a test sequence having at least one DC block, where the block is designed to provide specific information about a status of a redox mediator during the electrochemical analysis. In particular, the information relates to $M_{ox}$ and $M_{red}$ features (or even ratios thereof) during the electrochemical analysis.

Figure 3:
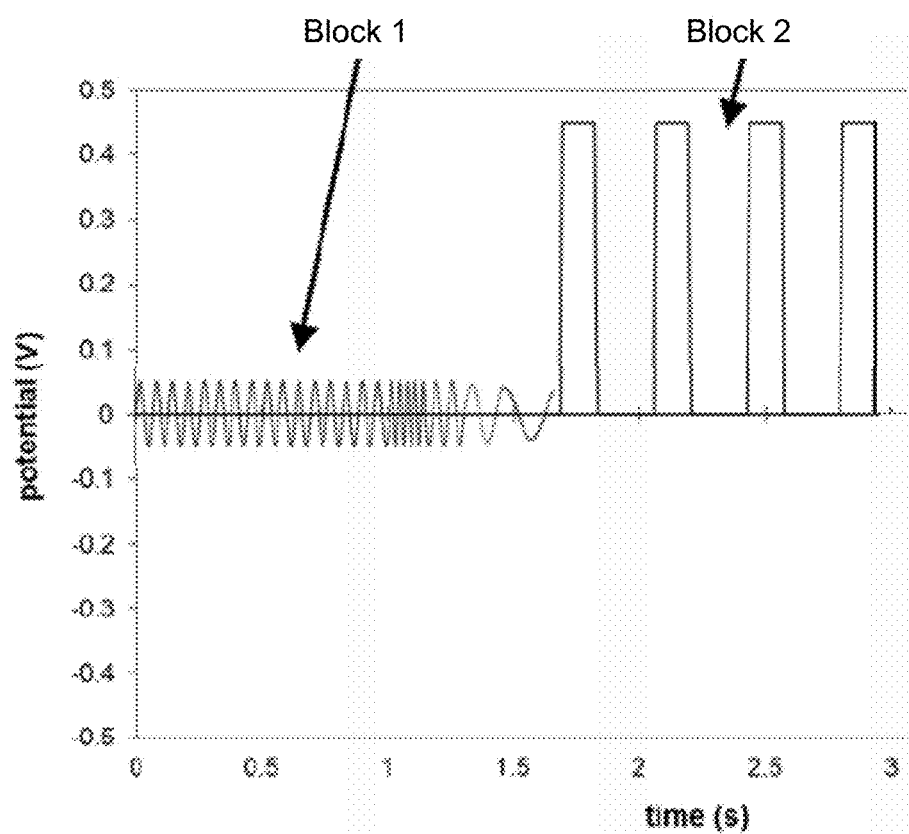
FIG. 3 shows an exemplary test sequence that may be employed by an analyte measurement device, apparatus or system.

The methods generally include applying to a fluidic sample, such as a body fluid, a test sequence having at least one DC block and measuring the DC current responses. Alternatively, the methods can include applying a test sequence also having an AC block in connection with at least one DC block and measuring the AC and DC current responses. FIG. 3 shows an exemplary test sequence that may be utilized in connection with SMBGs and other test systems. The test sequence can include two blocks, where, for example, one block includes low-amplitude AC signals followed by a controlled, DC block.

When part of the test sequence, the AC block can include a plurality of AC segments such as, for example, from about 2 segments to about 10 segments, from about 3 segments to about 9 segments, from about 4 segments to about 8 segments, from about 5 segments to about 7 segments, or about 6 segments. In other instances, the AC block can include about 2 segments, about 3 segments, about 4 segments, about 5 segments, about 6 segments, about 7 segments, about 8 segments, about 9 segments, or about 10 segments. In still other instances, the AC block can have more than 10 segments, that is, about 15 segments, about 20 segments, or about 25 segments. In yet other instances, the AC block can include 1 segment, where the segment has multiple low-frequency AC signals applied simultaneously.

One of skill in the art understands that the number of AC segments will be limited by the complexity of the response, the associated frequency range and time available to perform the measurements. Higher frequencies generally require high bandwidth electronics and faster sampling, whereas lower frequencies take longer and are typically noisier. The maximum number of segments therefore will be a compromise of these parameters, choosing the minimum count and frequency span needed to discriminate the sample and environmental and/or interferents of interest.

As used herein, "about" means within a statistically meaningful range of a value or values such as a stated concentration, length, molecular weight, pH, potential, time frame, temperature, voltage or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The frequency of each signal in each segment of the AC block can be from about 1 kHz to about 20 kHz, from about 2 kHz to about 19 kHz, from about 3 kHz to about 18 kHz, from about 4 kHz to about 17 kHz, from about 5 kHz to about 16 kHz, from about 6 kHz to about 15 kHz, from about 7 kHz to about 14 kHz, from about 8 kHz to about 13 kHz, from about 9 kHz to about 12 kHz or from about 10 kHz to about 11 kHz. In other instances, the frequency of each segment in the AC block can be about 1 kHz, about 2 kHz, about 3 kHz, about 4 kHz, about 5 kHz, about 6 kHz, about 7 kHz, about 8 kHz, about 9 kHz, about 10 kHz, about 11 kHz, about 12 kHz, about 13 kHz, about 14 kHz, about 15 kHz, about 16 kHz, about 17 kHz, about 18 kHz, about 19 kHz, or about 20 kHz. In still other instances, the frequency of each signal in each segment of the AC block can be more than 20 kHz, that is, about 30 kHz, about 40 kHz, or about 50 kHz. In some instances, one or more of the segments can have the same frequency, whereas in other instances each segment has a distinct frequency from the other segments. Four frequencies, however, generally is adequate. The exact frequencies employed can be readily generated by simple integer division of a measurement system clock's maximum frequency.

A maximum frequency limit for a signal in a segment of the AC block, however, can be up to about 100 kHz for an inexpensive, battery-powered handheld instrument. Beyond that, the increasing demands on analog bandwidth, sampling rate, storage and processing speed quickly add up, while the imaginary portion of a typical biosensor response becomes increasingly smaller with frequency. Lower frequencies have longer periods and take longer times to sample with comparable accuracy.

The AC block typically includes at least two different low-amplitude signals. For example, the AC block can include two (2) segments at two (2) frequencies such as, for example, about 10 kHz or about 20 kHz followed by about 1 kHz or about 2 kHz. In other instances, the AC block includes a plurality of low-amplitude signals. For example, the AC block can have five (5) segments at four (4) frequencies such as, for example, about 10 kHz, about 20 kHz, about 10 kHz, about 2 kHz and about 1 kHz. Alternatively, the AC block can have four (4) segments at four (4) frequencies such as, for example, about 20 kHz, about 10 kHz, about 2 kHz and about 1 kHz. Alternatively, the AC block can have four (4) frequencies applied simultaneously at about 10 kHz, about 20 kHz, about 10 kHz, about 2 kHz and about 1 kHz. Alternately still, the AC block can have a multi-frequency excitation waveform that simultaneously applies the desired low-amplitude AC signals. The AC frequencies may be applied sequentially, or combined and applied simultaneously and analyzed via Fourier Transform.

The AC block can be applied for about 500 msec to about 1.5 sec, about 600 msec to about 1.25 sec, about 700 msec to about 1 sec, or about 800 msec to about 900 msec. Alternatively, the AC block can be applied for about 500 msec, about 600 msec, about 700 msec, about 800 msec, about 900 msec, about 1 sec, about 1.25 sec or about 1.5 sec. In particular, AC block is applied for about 100 msec to about 300 msec.

One of skill in the art, however, understands that the number, frequency, duration and order of the AC segments can be varied.

AC current response information can be obtained at any time during a test sequence. Impedance results at lower frequencies may be influenced by analyte concentration if obtained after an electrochemical cell is DC polarized. In some instances, a series of AC current response measurements can be obtained early in the test sequence. Measurements taken shortly after a fluidic sample is applied to a biosensor will be influenced by diffusion, temperature and reagent solubility. In other instances, the AC response current measurements can be obtained at a sufficient time after an adequate sample has been applied to allow the response to stabilize, and avoid the transient response in the first second. Likewise, response current measurements can be made at one or more frequencies. Due to their capacitive nature, multiple AC measurements separated by a frequency octave or decade may offer different sensitivities or easier manipulation.

Additional details regarding exemplary AC blocks in electrochemical measurement methods are disclosed in, for example, U.S. Pat. Nos. 7,338,639; 7,390,667; 7,407,811; 7,417,811; 7,452,457; 7,488,601; 7,494,816; 7,597,793; 7,638,033; 7,751,864; 7,977,112; 7,981,363; 8,148,164; 8,298,828; 8,377,707 and 8,420,404.

With respect to the at least one DC block, it can include a constantly applied potential difference that alternates between about 0 mV and a predetermined positive potential difference, or other slowly time-varying potential difference that can be analyzed by traditional DC electrochemical methods. One of skill in the art, however, understands that the range for the applied potential difference can, and will, vary depending upon the analyte and reagent chemistry used.

The DC block can include a plurality of pulses such as, for example, from about 2 pulses to about 10 pulses, from about 3 pulses to about 9 pulses, from about 4 pulses to about 8 pulses, from about 5 pulses to about 7 pulses, or about 6 pulses. In other instances, the DC block can include about 2 pulses, about 3 pulses, about 4 pulses, about 5 pulses, about 6 pulses, about 7 pulses, about 8 pulses, about 9 pulses, or about 10 pulses. In still other instances, the DC block can have more than 10 pulses, that is, about 15 pulses, about 20 pulses, or about 25 pulses. As used herein, "pulse" means at least one excitation and/or one recovery period. The number of pulses, however, typically is limited by the available time for the test sequence. Shorter durations probe further from the electrode surface, and increase sensitivity to reagent thickness and diffusion modifiers.

The potential of each pulse in the DC block can be from about 0 mV to about 450 mV, from about 10 mV to about 425 mV, from about 15 mV to about 400 mV, from about 20 mV to about 375 mV, from about 25 mV to about 350 mV, from about 30 mV to about 325 mV, from about 35 mV to about 300 mV, from about 40 mV to about 275 mV, from about 45 mV to about 250 mV, from about 50 mV to about 225 mV, from about 75 mV to about 200 mV, from about 100 mV to about 175 mV, or from about 125 mV to about 150 mV. In other instances, the potential of each pulse in the DC block can be about 1 mV, about 10 mV, about 15 mV, about 20 mV, about 25 mV, about 30 mV, about 35 mV, about 40 mV, about 45 mV, about 50 mV, about 60 mV, about 70 mV, about 80 mV, about 90 mV, about 100 mV, about 110 mV, about 120 mV, about 130 mV, about 140 mV, about 150 mV, about 160 mV, about 170 mV, about 180 mV, about 190 mV, about 200 mV, about 210 mV, about 220 mV, about 230 mV, about 240 mV, about 250 mV, about 260 mV, about 270 mV, about 280 mV, about 290 mV, about 300 mV, about 310 mV, about 320 mV, about 330 mV, about 340 mV, about 350 mV, about 360 mV, about 370 mV, about 380 mV, about 390 mV, about 400 mV, about 410 mV, about 420 mV, about 430 mV, about 440 mV, or about 450 mV. In still other instances, the potential of each pulse of the DC block can be more than 450 mV, that is, about 475 mV, about 500 mV, about 525 mV, about 550 mV, about 575 mV, about 600 mV kHz, about 625 mV, about 650 mV, about 675 mV, about 700 mV, about 725 mV, or about 750 mV. In still other instances, the excitation pulse potential can be greater-than, less-than or equal to about +450 mV. In some instances, one or more of the pulses can have the same potential, whereas in other instances each pulse has a distinct potential from the other pulses.

As noted above, the applied DC potential can be fixed at about 0 mV between excitation pulses to provide a recovery pulse, thus making it a generally continuous excitation waveform. This is in contrast to a test signal sequence from known techniques that prescribe the use of an open circuit between positive DC pulses, thereby excluding the possibility of collecting and analyzing the current between positive pulses.

Regardless of the number, each DC pulse can be applied for about 50 msec to about 500 msec, about 60 msec to about 450 msec, about 70 msec to about 400 msec, about 80 msec to about 350 msec, about 90 msec to about 300 msec, about 100 msec to about 250 msec, about 150 msec to about 200 msec, or about 175 msec. Alternatively, each pulse can be applied for about 50 msec, about 60 msec, about 70 msec, about 80 msec, about 90 msec, about 100 msec, about 125 msec, about 150 msec, about 175 msec, about 200 msec, about 225 msec, about 250 msec, about 275 msec, about 300 msec, about 325 msec, about 350 msec, about 375 msec, about 400 msec, about 425 msec, about 450 msec, about 475 msec or about 500 msec. In particular, each DC pulse at +450 mV can be applied for about 250 msec, and each DC pulse at 0 mV can be applied for about 500 msec. Alternatively still, each pulse can be applied for less than about 50 msec or more than about 500 msec. The duration should be long enough or the onset soft enough to avoid charging currents. Regardless, the pulse duration should be applied long enough to enable reasonable 50/60 Hz noise rejection. Moreover, the time between pulses is ideally long enough to allow the electrochemical cell to discharge and return close to its pre-pulse state. Furthermore, the operating potential will depend upon the mediator and measurement system. The examples herein demonstrate proof-of-principal with NA-derived redox mediator.

Generally, the ramp rate of each DC pulse is selected to provide about 50% or greater reduction in peak current relative to the peak current provided by a nearly ideal potential transition. In some instances, each pulse can have the same ramp rate. In other instances, some pulses can have the same ramp rate and other pulses can have a different ramp rate. In still other instances, each pulse has its own ramp rate. For example, effective ramp rates can be from about 5 mV/msec to about 75 mV/msec or from about 10 mV/msec to about 50 mV/msec, 15 mV/msec to about 25 mV/msec, or about 20 mV/msec. Alternatively, the ramp rate can be about 5 mV/msec, about 10 mV/msec, about 15 mV/msec, about 20 mV/msec, about 25 mV/msec, about 30 mV/msec, about 35 mV/msec, about 40 mV/msec, about 45 mV/msec, about 50 mV/msec, about 55 mV/msec, about 60 mV/msec, about 65 mV/msec, about 70 mV/msec, or about 75 mV/msec. In particular, the ramp rate can be from about 40 mV/msec to about 50 mV/msec.

To determine the excitation potential for a given redox mediator, one may plot current measured a fixed time after a selected working electrode/counter-electrode (WE-CE) potential step is applied (e.g., 3.5 sec). In any case, one of skill in the art would strive to operate comfortably on a current-potential plateau. Higher potentials, however, are not always better as they can invite other (i.e., interfering) reactions that may undesirably contribute to the analyte measurement of interest.

In some instances, the test sequence includes a single DC block, whereas in other instances the test sequence includes two or more DC blocks.

An exemplary DC block can alternate (i.e., pulse) between about 0 mV and about +450 mV (in biamperometric mode).

Like the AC block, one of skill in the art understands that the number, potential, duration and order of the DC pulses can be varied.

In the methods, the AC and/or DC response current information can be obtained (i.e., measured or recorded) at about 2,000/sec to about 200,000/sec, at about 3,000/sec to about 190,000/sec, at about 4,000/sec to about 180,000/sec, at about 5,000/sec to about 170,000, at about 6,000/sec to about 160,000/sec, at about 7,000/sec to about 150,000/sec, at about 8,000/sec to about 140,000/sec, at about 9,000/sec to about 130,000/sec, at about 10,000/sec to about 120,000/sec, at about 15,000/sec to about 110,000/sec, at about 20,000/sec to about 100,000/sec, at about 30,000/sec to about 90,000/sec, at about 40,000/sec to about 80,000/sec, at about 50,000/sec to about 70,000/sec, or at about 60,000/sec. In some instances, the AC and/or DC response current information can be obtained at about 100/sec to about 200/sec, at about 200/sec to about 300/sec, at about 300/sec to about 400/sec, at about 400/sec to about 500/sec, at about 500/sec to about 600/sec, at about 600/sec to about 700/sec, at about 700/sec to about 800/sec, at about 800/sec to about 900/sec, at about 1,000/sec to about 1,500/sec, at about 1,500/sec to about 2,000/sec, at about 2,000/sec to about 2,500/sec, at about 2,500/sec to about 3,000/sec, at about 3,000/sec to about 3,500/sec, at about 3,500/sec to about 4,000/sec, at about 4,000/sec to about 4,500/sec, at about 4,500/sec to about 5,000/sec, at about 5,000/sec to about 5,500/sec to about 6,000/sec, at about 6,000/sec to about 6,500/sec, at about 6,500 to about 7,000/sec, at about 7,000/sec to about 7,500/sec, at about 7,500/sec to about 8,000/sec, at about 8,000/sec to about 8,500/sec, at about 8,500 to about 9,000/sec, at about 9,000/sec to about 9,500/sec, at about 9,500/sec to about 10,000/sec, at about 10,000/sec to about 20,000/sec, at about 20,000/sec to about 30,000/sec, at about 30,000/sec to about 40,000/sec, at about 40,000/sec to about 50,000/sec, at about 50,000/sec to about 60,000/sec, at about 60,000/sec to about 70,000/sec, at about 70,000/sec to about 80,000/sec, at about 80,000/sec to about 90,000/sec, at about 90,000/sec to about 100,000/sec, at about 100,000/sec to about 110,000/sec, at about 110,000/sec to about 120,000/sec, at about 120,000/sec to about 130,000/sec, at about 130,000/sec to about 140,000/sec, at about 140,000/sec to about 150,000/sec, at about 150,000/sec to about 160,000/sec, at about 160,000/sec to about 170,000/sec, at about 170,000/sec to about 180,000/sec, at about 180,000/sec to about 190,000/sec, or at about 200,000/sec. In other instances, the AC and/or DC response current information can be obtained up to about 100/sec, about 200/sec, about 300/sec, about 400/sec, about 500/sec, 600/sec, about 700/sec, about 800/sec, about 900/sec, about 1,000/sec, about 1,250/sec, about 1,500/sec, about 1,750/sec, about 2,000/sec, about 2,225/sec, about 2,500/sec, about 2,750/sec, about 3,000/sec, about 3,250/sec, about 3,500/sec, about 3,750/sec, about 4,000/sec, about 4,250/sec, about 4,500/sec, about 4,750/sec, about 5,000/sec, about 5,250/sec, about 5,500/sec, about 5,750/sec, about 6,000/sec, about 6,250/sec, about 6,500, about 7,000/sec, about 7,250/sec, about 7,500/sec, about 7,750/sec, about 8,000/sec, about 8,250/sec, about 8,500/sec, about 8,750, about 9,000/sec, about 9,250/sec, about 9,500/sec, about 9,750/sec, about 10,000/sec, about 15,000/sec, about 20,000/sec, about 25,000/sec, about 30,000/sec, about 35,000/sec, about 40,000/sec, about 45,000/sec, about 50,000/sec, about 55,000/sec, about 60,000/sec, about 65,000/sec, about 70,000/sec, about 75,000/sec, about 80,000/sec, about 85,000/sec, about 90,000/sec, about 95,000/sec, about 100,000/sec, about 105,000/sec, about 110,000/sec, about 115,000/sec, about 120,000/sec, about 125,000/sec, about 130,000/sec, about 135,000/sec, about 140,000/sec, about 145,000/sec, about 150,000/sec, about 155,000/sec, about 160,000/sec, about 165,000/sec, about 170,000/sec, about 175,000/sec, about 180,000/sec, about 185,000/sec, about 190,000/sec, about 195,000 or at about 200,000/sec. In yet other instances, the AC and/or DC response current information can be obtained at more than 200,000/sec.

AC and/or DC current response information can be collected from the test sequence and includes current responses to the AC and DC blocks. In some instances, the current response information can be collected at an A/D sampling rate for DC and AC measurements to simplify the system design, including a single shared signal path for AC and DC measurements. Common digital audio sampling rates range include, but are not limited to, from about 44.1 kHz to about 192 kHz. A/D converters in this range are readily available from variety of commercial semiconductor suppliers.

Current response information (e.g., duration, shape and/or magnitude) to the AC block may be used for determining admittance and phase values or other complex parameters as described in further detail below. Current response information to this DC block can be used for measuring an analyte such as glucose or another analyte subject to analysis through oxidation/reduction techniques. In addition, the current response information also can be used to examine for Hct and temperature effects on the analyte concentration.

In some instances, the AC block can be applied before the at least one DC block, after the at least DC block, or interspersed therewith. Alternatively, the AC block is applied before the at least one DC sequence.

Thus, an exemplary test sequence can include: (1) an AC block of a plurality of low-amplitude AC signals; and (2) a DC block of short-duration (e.g., about 50-500 msec) about +450-mV pulses separated by similarly short-duration (e.g., about 50-500 msec) recovery pulses during which a closed circuit about 0-mV recovery potential is applied.

In the methods, a closed circuit, about 0 mV DC potential is applied to provide a recovery pulse, thus making it a continuous excitation potential profile. This is in contrast to the use of an open circuit between non-zero DC pulses. The use of a recovery pulse allows the collection and analysis of response currents during the duration of the recovery pulses in addition to the current response information during non-zero pulses. The recovery pulse, can be viewed as an adequately long recovery period in which at least part of the electrochemical reaction with an analyte such as glucose is turned off, thereby allowing the system to return to a common starting point before subsequent interrogation with another non-zero pulse.

Once the response information is collected, the methods then include providing a statistical antioxidant failsafe using either a classifier or a discriminator that distinguishes between samples containing antioxidant levels with less than a predetermined concentration from samples that have antioxidant levels that are greater than the predetermined concentration. The failsafe functionality can be used with an electrochemical system that can provide impedance characteristics of the cell and pulsed amperometric measurements that are unipolar or bipolar. It also can be used in electrochemical systems where the electrochemical cell is simultaneously excited with broad-band frequencies and DC pulsing of unipolar or bipolar form. The failsafe function may be utilized in connection with test systems configured to determine concentration of a number of different analytes. In some instances, the failsafe may be used in conjunction with a glucose test system such as an SMBG system. If the failsafe identifies the sample to have a safe antioxidant level at which the calculated glucose concentration would be reliable, the user may be presented with the calculated glucose concentration. Otherwise, the user may be presented with an error code indicating that the antioxidant level or other interferent exceeds a threshold at which a reliable glucose concentration can be delivered. For example, the predetermined threshold for ascorbate in a sample can be about 3 mg/dL or higher, about 4 mg/dL or higher, about 5 mg/dL or higher, about 6 mg/dL or higher, about 7 mg/dL or higher, about 8 mg/dL or higher, about 9 mg/dL or higher or about 10 mg/dL or higher.

With respect to the statistic-based antioxidant failsafe, it can be a discriminator that distinguishes between samples containing antioxidant levels, such as ascorbate, with less than 10 mg/dL from samples having levels that are greater than 10 mg/dL. It shall be appreciated that the 10 mg/dL is exemplary and that other thresholds may also be utilized depending on the sensitivity of the test system to the presence of the antioxidant of interest. The failsafe may be constructed in accordance with the following equation:

$$\text{Probability(Ascorbate} > T1) = \frac{\sum_{i=1}^{M} \alpha_i \cdot \tanh\left(\sum_{j=1}^{N} \beta_j \cdot O_j\right)}{1 + \sum_{i=1}^{M} \alpha_i \cdot \tanh\left(\sum_{j=1}^{N} \beta_j \cdot O_j\right)}.$$

The determined value of the nonlinear function of this equation may be used to identify the probability that the sample belongs to one of the two classes of samples. The failsafe is activated if Probabiltiy(Ascorbate>T1) is greater than T2 where T2 is in the interval [0, 1]. The quantities denoted by $O_j$ are the AC admittance values $Y_{20}, Y_{10}, Y_2$ and $Y_1$, and phase values $P_{20}, P_{10}, P_2$ and $P_1$, which are based upon current response information from the section labeled "AC Block" and the DC quantities that are obtained from the section labeled "DC Block" in FIG. 3. The quantities denoted by $\beta_j$, and $\alpha_i$ are constants (parameters) that are estimated with suitable training data.

Conceptually, this method alters the statement of the problem as it relates to an antioxidant failsafe. Instead of quantitatively determining the antioxidant level, and whether it is above a threshold, these methods determine whether the measurements from the DC Block are consistent with a low or high antioxidant level. In other words, the problem is converted from one of discrete antioxidant quantitation to one of antioxidant classification or discrimination. It should be noted that this failsafe can be based on DC response info from as few as only the first 3 "pulses" in the DC Block of FIG. 3 (i.e., excitation-recovery-excitation), thereby significantly reducing the test time, provided the current response data from these 3 pulses is sufficient also for determining or otherwise calculating an analyte concentration (e.g., blood glucose). Thus, for example, in FIG. 3 the total time for the potential sequence is as low as 2.5 sec. It will be appreciated by one of skill in the art that suitable algorithms may be created that use as much or as little current response data from as many pulses as will be deemed sufficient for purposes of the analyte determination and interferent failsafe determination.

Figure 4:
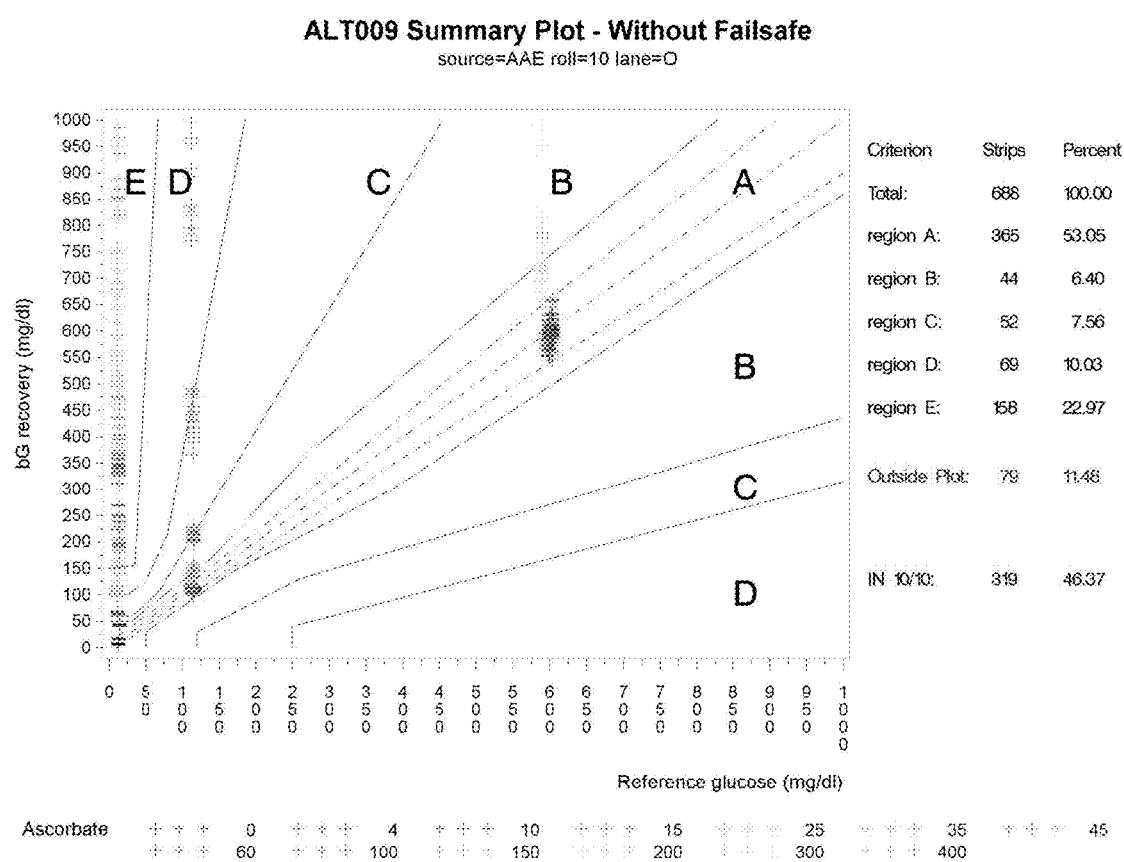
FIG. 4 is a graph of exemplary test results without an antioxidant (e.g., ascorbate) failsafe.

With reference to FIG. 4, a graph is shown of test system performance without an antioxidant (i.e., ascorbate) failsafe. The horizontal axis of the graph indicates reference glucose in mg/dL (i.e., the actual concentration of glucose in a controlled sample). The vertical axis of the graph indicates bG recovery in mg/dL (i.e., the value of the bG measurement determined by the test system). The coding of the data points represented by + symbols indicates the ascorbate concentration of the sample in mg/dL (0, 4, 10, 15, 25, 35, 45, 60, 80, 100, 150, 200, 300 and 400). The vertical groupings of + symbols indicate measurement results for samples spiked with specific glucose concentrations, namely 25 mg/dL (left grouping), 125 mg/dL (center grouping) and 600 mg/dL (right grouping).

In FIG. 4, Parkes region A represents measurements for which a bG measurement by the test system is acceptably accurate. More specifically, Parkes region A indicates that the measurement has no effect on clinical outcome, Parkes region B indicates an altered clinical action with little or no effect on clinical outcome, Parkes region C indicates an altered clinical action likely to effect clinical outcome, Parkes region D indicates an altered clinical action that could have significant medical risk, and Parkes region E indicates an altered clinical action that could have dangerous consequences. It also should be noted that the dashed lines within Parkes region A represent actual 10/10 operation.

In FIG. 4, however, there are numerous measurements for all tested blood glucose levels that fall outside Parkes region A and that include inaccurate test results. The specific results are listed in Table 1 below.

TABLE 1

| Criterion | Number of Strips | Percent |
| --- | --- | --- |
| Total | 668 | 100 |
| Region A | 365 | 53.05 |
| Region B | 44 | 6.4 |
| Region C | 52 | 7.56 |
| Region D | 69 | 10.03 |
| Region E | 158 | 22.97 |
| Outside Plot | 79 | 11.48 |
| In 10/10 region | 319 | 46.37 |

Figure 5:
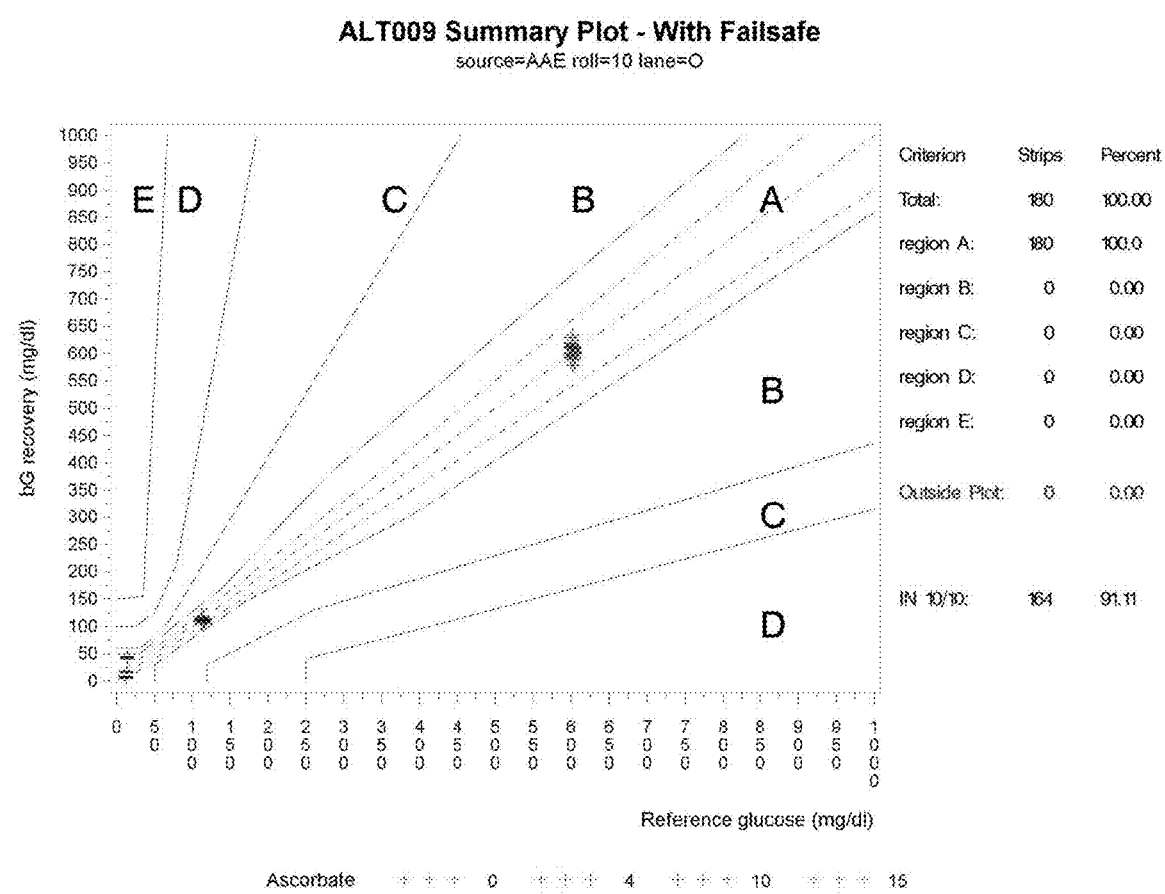
FIG. 5 is a graph of exemplary test results with an antioxidant ascorbate failsafe.

With reference to FIG. 5, a plot is shown of test system performance with a statistical antioxidant (i.e., ascorbate) failsafe activated. The horizontal axis of the graph indicates reference glucose in mg/dL (i.e., the actual concentration of glucose in a controlled sample). The vertical axis of the graph indicates bG recovery in mg/dL (i.e., the value of the bG measurement determined by the test system). The coding of the data points represented by + symbols indicates the antioxidant concentration of the sample in mg/dL (0, 4, 10, 15 and 80). The vertical groupings of + symbols indicate measurement results for samples spiked with specific glucose concentrations, namely 25 mg/dL (left grouping), 125 mg/dL (center grouping) and 600 mg/dL (right grouping). Parkes regions A, B, C, D and E provide the same indications described above in connection with FIG. 4. As shown in FIG. 5, all bG measurements are within region A thus demonstrating 10/10 operation. The specific results are listed in Table 2 below.

TABLE 2

| Criterion | Number of Strips | Percent |
| --- | --- | --- |
| Total | 180 | 100 |
| Region A | 180 | 100 |
| Region B | 0 | 0.00 |
| Region C | 0 | 0.00 |
| Region D | 0 | 0.00 |
| Region E | 0 | 0.00 |
| Outside Plot | 0 | 0.00 |
| In 10/10 region | 164 | 91.11 |

Tables 3 and 4 below illustrate additional information relating to FIGS. 4-5, respectively.

TABLE 3

| Target Glucose (mg/dL) | Ascorbate (mg/dl) | Without Failsafe Activated | | | | |
| --- | --- | --- | --- | --- | --- | --- |
| | | Parkes Region | | | | |
| | | A | B | C | D | E |
| 10 | 0 | 32 | 0 | 0 | 0 | 0 |
| | 4 | 16 | 0 | 0 | 0 | 0 |
| | 10 | 16 | 0 | 0 | 0 | 0 |
| | 15 | 0 | 0 | 16 | 0 | 0 |
| | 25 | 0 | 0 | 1 | 15 | 0 |
| | 35 | 0 | 0 | 0 | 5 | 11 |
| | 45 | 0 | 0 | 0 | 0 | 16 |
| | 60 | 0 | 0 | 0 | 0 | 32 |
| | 100 | 0 | 0 | 0 | 0 | 16 |
| | 150 | 0 | 0 | 0 | 0 | 16 |
| | 200 | 0 | 0 | 0 | 0 | 16 |
| | 300 | 0 | 0 | 0 | 0 | 16 |
| | 400 | 0 | 0 | 0 | 0 | 16 |
| 120 | 0 | 32 | 0 | 0 | 0 | 0 |
| | 4 | 16 | 0 | 0 | 0 | 0 |
| | 10 | 16 | 0 | 0 | 0 | 0 |
| | 15 | 15 | 1 | 0 | 0 | 0 |
| | 25 | 16 | 0 | 0 | 0 | 0 |

TABLE 3-continued

| Target Glucose (mg/dL) | Ascorbate (mg/dl) | Without Failsafe Activated Parkes Region | | | | |
|---|---|---|---|---|---|---|
| | | A | B | C | D | E |
| | 35 | 15 | 1 | 0 | 0 | 0 |
| | 45 | 5 | 11 | 0 | 0 | 0 |
| | 60 | 0 | 10 | 6 | 0 | 0 |
| | 100 | 0 | 0 | 12 | 4 | 0 |
| | 150 | 0 | 0 | 0 | 16 | 0 |
| | 200 | 0 | 0 | 0 | 16 | 0 |
| | 300 | 0 | 0 | 0 | 13 | 3 |
| | 400 | 0 | 0 | 0 | 0 | 16 |
| 600 | 0 | 32 | 0 | 0 | 0 | 0 |
| | 4 | 16 | 0 | 0 | 0 | 0 |
| | 10 | 16 | 0 | 0 | 0 | 0 |
| | 15 | 16 | 0 | 0 | 0 | 0 |
| | 25 | 16 | 0 | 0 | 0 | 0 |
| | 35 | 16 | 0 | 0 | 0 | 0 |
| | 45 | 16 | 0 | 0 | 0 | 0 |
| | 60 | 16 | 0 | 0 | 0 | 0 |
| | 100 | 16 | 0 | 0 | 0 | 0 |
| | 150 | 16 | 0 | 0 | 0 | 0 |
| | 200 | 10 | 6 | 0 | 0 | 0 |
| | 300 | 0 | 15 | 1 | 0 | 0 |
| | 400 | 0 | 0 | 16 | 0 | 0 |

TABLE 4

| Target Glucose (mg/dL) | Ascorbate (mg/dl) | With Failsafe Activated Parkes Region | | | | |
|---|---|---|---|---|---|---|
| | | A | B | C | D | E |
| 10 | 0 | 32 | 0 | 0 | 0 | 0 |
| | 4 | 16 | 0 | 0 | 0 | 0 |
| | 10 | 16 | 0 | 0 | 0 | 0 |
| | 15 | 0 | 0 | 0 | 0 | 0 |
| | 25 | 0 | 0 | 0 | 0 | 0 |
| | 35 | 0 | 0 | 0 | 0 | 0 |
| | 45 | 0 | 0 | 0 | 0 | 0 |
| | 60 | 0 | 0 | 0 | 0 | 0 |
| | 100 | 0 | 0 | 0 | 0 | 0 |
| | 150 | 0 | 0 | 0 | 0 | 0 |
| | 200 | 0 | 0 | 0 | 0 | 0 |
| | 300 | 0 | 0 | 0 | 0 | 0 |
| | 400 | 0 | 0 | 0 | 0 | 0 |
| 120 | 0 | 32 | 0 | 0 | 0 | 0 |
| | 4 | 16 | 0 | 0 | 0 | 0 |
| | 10 | 16 | 0 | 0 | 0 | 0 |
| | 15 | 0 | 0 | 0 | 0 | 0 |
| | 25 | 0 | 0 | 0 | 0 | 0 |
| | 35 | 0 | 0 | 0 | 0 | 0 |
| | 45 | 0 | 0 | 0 | 0 | 0 |
| | 60 | 0 | 0 | 0 | 0 | 0 |
| | 100 | 0 | 0 | 0 | 0 | 0 |
| | 150 | 0 | 0 | 0 | 0 | 0 |
| | 200 | 0 | 0 | 0 | 0 | 0 |
| | 300 | 0 | 0 | 0 | 0 | 0 |
| | 400 | 0 | 0 | 0 | 0 | 0 |
| 600 | 0 | 16 | 0 | 0 | 0 | 0 |
| | 4 | 16 | 0 | 0 | 0 | 0 |
| | 10 | 16 | 0 | 0 | 0 | 0 |
| | 15 | 4 | 0 | 0 | 0 | 0 |
| | 25 | 0 | 0 | 0 | 0 | 0 |
| | 35 | 0 | 0 | 0 | 0 | 0 |
| | 45 | 0 | 0 | 0 | 0 | 0 |
| | 60 | 0 | 0 | 0 | 0 | 0 |
| | 100 | 0 | 0 | 0 | 0 | 0 |
| | 150 | 0 | 0 | 0 | 0 | 0 |
| | 200 | 0 | 0 | 0 | 0 | 0 |
| | 300 | 0 | 0 | 0 | 0 | 0 |
| | 400 | 0 | 0 | 0 | 0 | 0 |

The tally tables show the number of observations from samples with different target glucoses and ascorbate interference levels that fall in each of the Parkes regions. Table 3 shows the counts when the ascorbate failsafe has not been activated, whereas Table 4 shows the counts when the ascorbate failsafe has been activated.

It also should be noted that the results shown in FIG. 5 would be substantially identical for the other embodiments described herein. It shall be appreciated that the foregoing description is on an exemplary statistical failsafe description and is not limiting.

A number of modifications and variations are contemplated, including: modifying the failsafe to improve the classification accuracy based on the ascorbate (or other interferent) level; altering the failsafe to differentiate between sample attributes that could lead to unsafe glucose observations (e.g., differentiating between Parkes region C, D and E); incorporating the ascorbate (or other interferent) level into an adjustment of the predicted glucose so the system can operate over a wider range of ascorbate levels; using machine learning approaches to reduce required memory, number of computations, and computation time; and utilizing the effect of transformed observables (AC and DC measurements) that include impedance forms, powers of ACs, and log-transformations of DCs.

Additionally, classifier or discriminator functionality may be provided in a number of forms, including: a classifier or discriminator that distinguishes the sample as belonging to one of two classes (e.g., safe/unsafe or pass/fail); a classifier or discriminator that distinguishes the sample as belonging to one of three classes (safe, unsafe if uncorrected, unsafe and uncorrectable); or other classifiers or discriminators effective to sort measurements into two or more categories associated with accurate and inaccurate measurements results. The classifier also may utilize a number of machine learning techniques including logistic functions, decision trees and support vector machines.

In analyte determination training, 4 observations in the ≤10 mg/dL class and 6 observations in the >10 mg/dL class were misclassified, corresponding to a classification accuracy of 99.98% and 99.47% for each class, respectively. These results are summarized in Table 5 below.

TABLE 5

Training set composition and performance for DC Block 1 classifier.

| Training Set | Predicted Ascorbate ≤10 mg/dL | Predicted Ascorbate >10 mg/dL | All |
|---|---|---|---|
| Actual Ascorbate ≤10 mg/dL | 24979 | 4 | 24982 |
| Actual Ascorbate >10 mg/dL | 6 | 1140 | 1146 |
| All | 24985 | 1144 | 26129 |

Application of the classifier based upon the DC Block resulted in the misclassification of 3 observations in the >10 mg/dL class, and 2 observations in the ≤10 mg/dL class, corresponding to an overall classification accuracy of 99.98% and 99.65 for each class, respectively. These results are summarized in Table 6 below.

TABLE 6

Independent test set composition and performance for DC Block 1 classifier.

| Independent Test Set | Predicted Ascorbate ≤10 mg/dL | Predicted Ascorbate >10 mg/dL | All |
|---|---|---|---|
| Actual Ascorbate ≤10 mg/dL | 12488 | 3 | 12491 |
| Actual Ascorbate >10 mg/dL | 2 | 572 | 574 |
| All | 12490 | 575 | 13065 |

Figure 6:
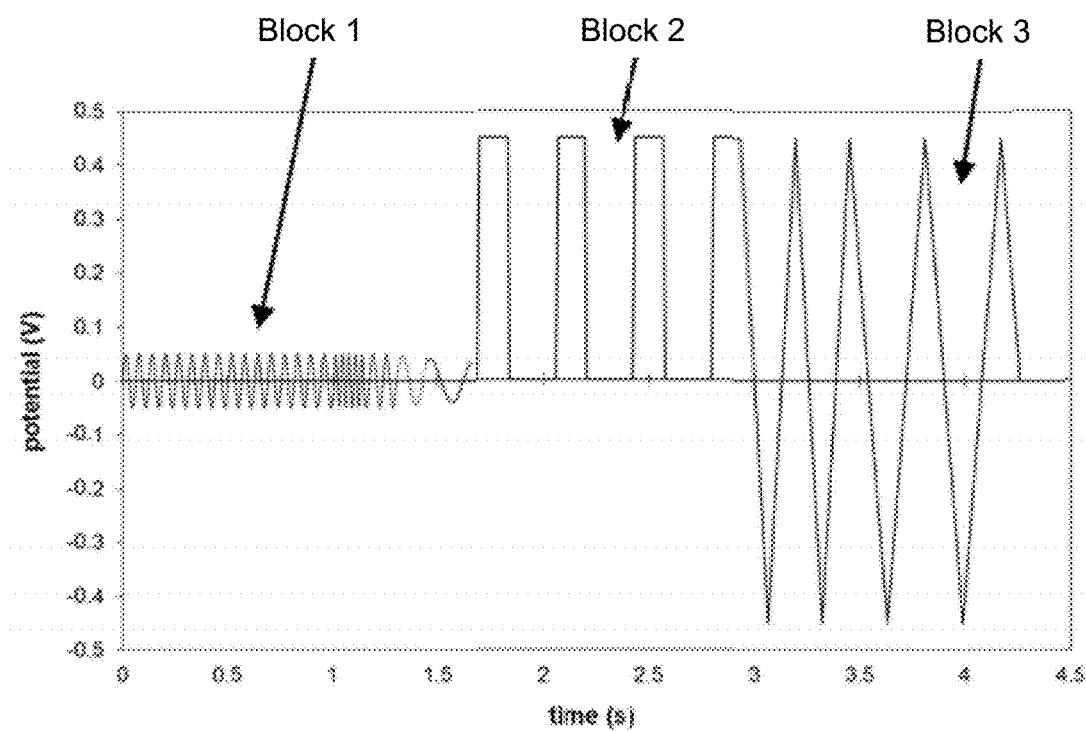
FIG. 6 shows another exemplary test sequence that may be employed by an analyte test system.

With reference to FIG. 6, another exemplary test sequence is shown that includes (1) an AC block (labeled AC Block) having a plurality of AC segments at different frequencies; (2) a DC block (labeled DC Block 1) having short, 450 mV pulses separated by relaxation potentials at 0 mV where the mediator is not oxidized by the applied potential; and (3) a second DC block (labeled DC Block 2) having a SRBP at two different ramp rates. More specifically, the AC block can have five (5) segments different at four (4) frequencies, namely 10 kHz, 20 kHz, 10 kHz, 2 kHz and 1 kHz segments. Current response information to the AC block may be utilized to determine admittance and phase values or other complex parameters as described in further detail below. In some instances, an analyte concentration determination, such as a bG determination, is performed based upon current response information from the AC block and current response information from DC Block 1. Current response information from DC Block 2 may be used for constructing a glucose failsafe.

The second DC block illustrated in FIG. 6 arose out of research relating to SRBP DC excitation sequences. In theory, any DC excitation with sufficient potential to cause an electrochemical reaction of mediator on the electrodes will produce a current response that can be used to quantitatively measure an analyte such as glucose. This current response also will be impacted by changing Hct and temperature levels. This research assessed the value of SRBP DC excitations sequences to determine whether additional, unique information could be obtained and used to improve analyte measurement system performance and/or capabilities, in much the same way that the use of recovery pulse information in combination with excitation pulse information can be utilized to improve performance.

The current response to the first AC Block of FIG. 6 does not contain information about glucose, but instead encodes information about hematocrit, temperature and other factors, which can be used to correct a bG reading derived from the DC test block(s). The current response to DC Block 1 corresponds primarily to the amount of PDA, which is proportional to the amount of glucose present. In contrast, the current response to DC Block 2 provides quantitative information about the levels of QDI, as well as PDA. Like DC Block 1, the current responses at +450-mV and −450-mV correspond to PDA, and are proportional to the amount of glucose present. However, the SRBP also enables the detection of QDI at lower, mid-range applied potentials during the negative- and positive-going applied potential ramps.

Figure 7:
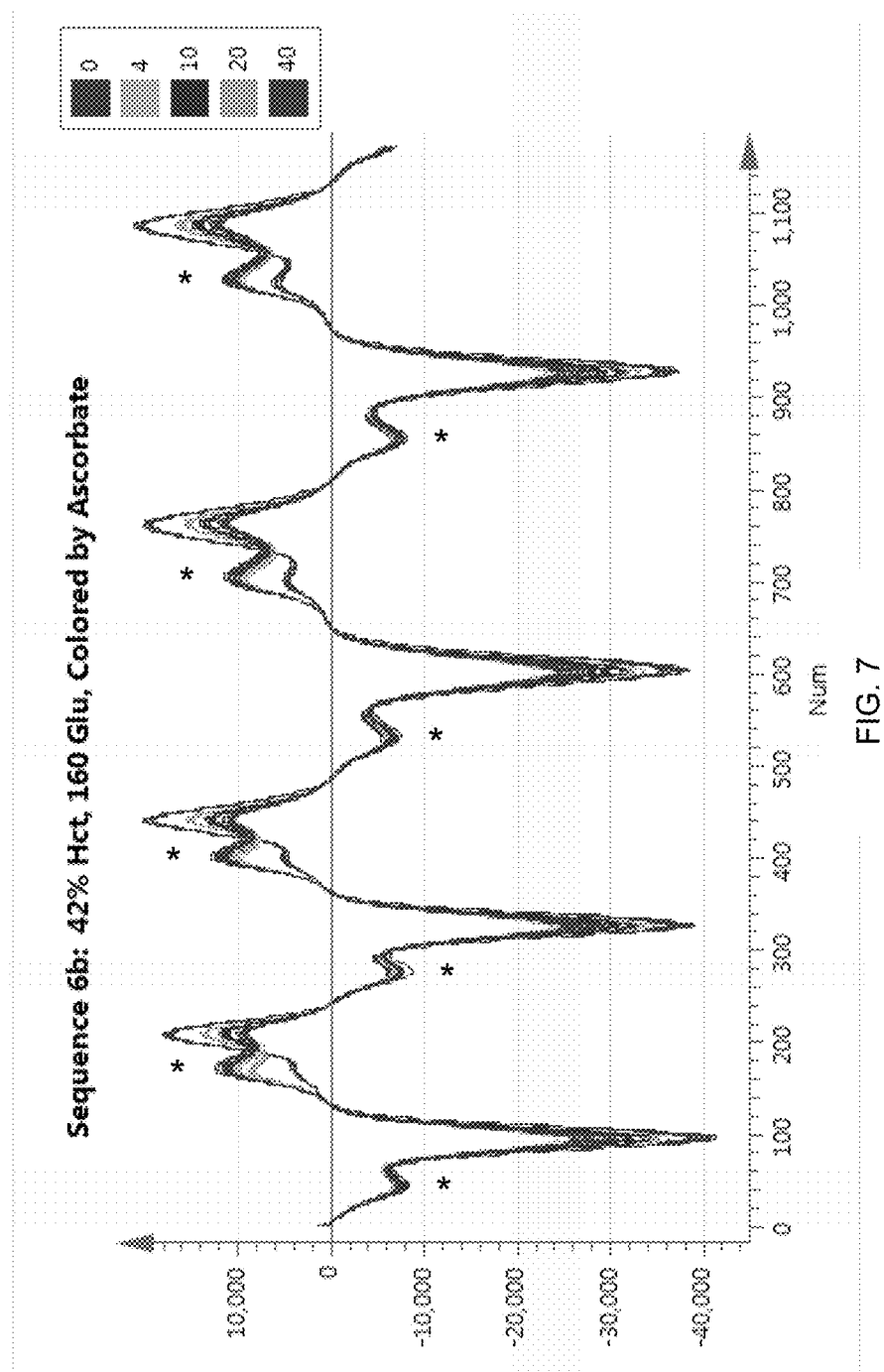
FIG. 7 shows current responses to a pulsed DC potential for multiple test samples with different levels of ascorbate.

With reference to FIG. 7, current responses are shown to the DC Block 2 potential for five different blood samples with different levels of ascorbate. Ascorbate reacts with QDI, resulting in a decrease of the QDI feature; the QDI feature for each potential sweep is denoted by an "*". As described above, ascorbate reacts rapidly with QDI and reduces it, thereby increasing the amount of PDA, resulting in a higher current being detected at the working electrode. Because the perceived higher current is assumed to be proportional to glucose, this results in a falsely-elevated glucose reading. It is important to understand that high ascorbate levels cause an increase in the PDA-related current responses in both DC Block 1 and DC Block 2.

It has been recognized that DC Block 2 provides information that can be used to detect high ascorbate and to produce a quantitative estimate of the ascorbate level. Because it is possible to quantitatively predict ascorbate, it follows that a cutoff at a particular ascorbate level can be used as a limit for failsafe implementation. If an ascorbate value is less than the established limit, then the bias in the predicted glucose value is deemed acceptable, and a bG value is delivered by the meter. However, if an ascorbate value is greater than the established limit, thereby resulting in an unsafe glucose estimate, only an error code may be delivered to the end user.

Figure 8:
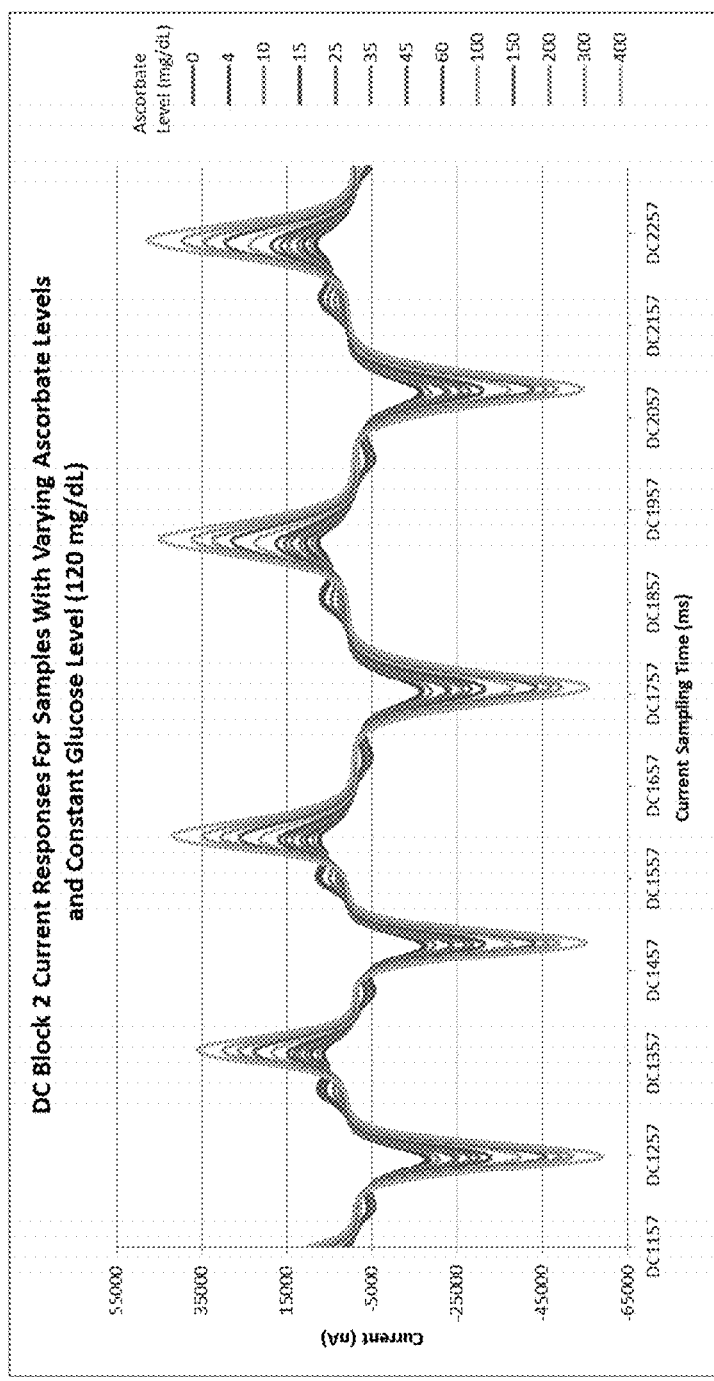
FIG. 8 shows current responses for a set of blood samples with ascorbate levels ranging from 0 mg/dL to 400 mg/dL and a glucose level of 120 mg/dL.

With reference to FIG. 8, current responses are shown to the DC Block 2 potentials for a set of blood samples with ascorbate levels ranging from 0 to 400 mg/dL. All of the samples have the same glucose level (120 mg/dL).

Figure 9:
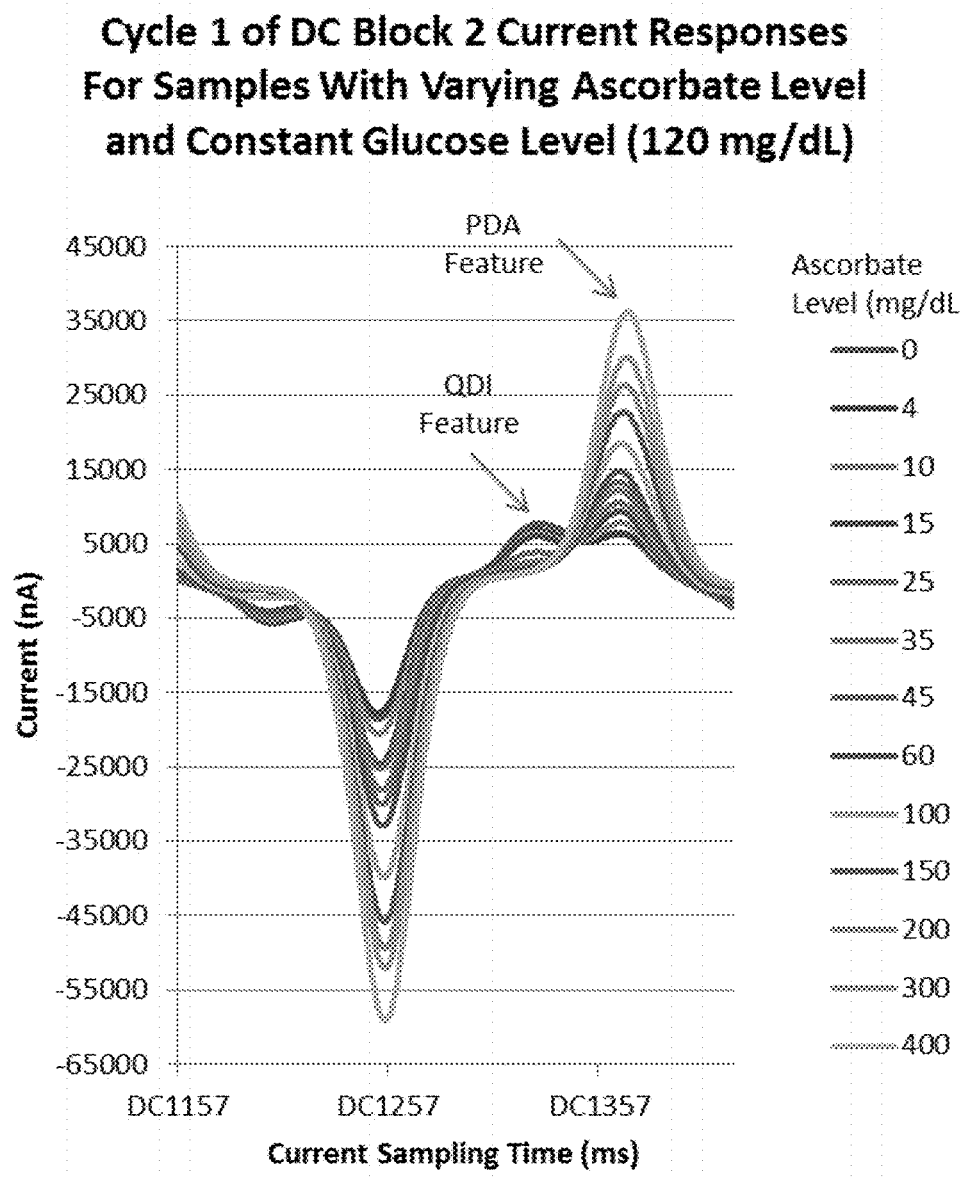
FIG. 9 shows a more detailed view of a portion of FIG. 8 highlighting a QDI feature and a PDA feature.

FIG. 9 shows a more detailed view of a portion of FIG. 8, specifically the first negative- and positive-going sweep of FIG. 8. The QDI feature and the PDA feature are both present in the current response information and vary as a function of ascorbate level.

Figure 10:
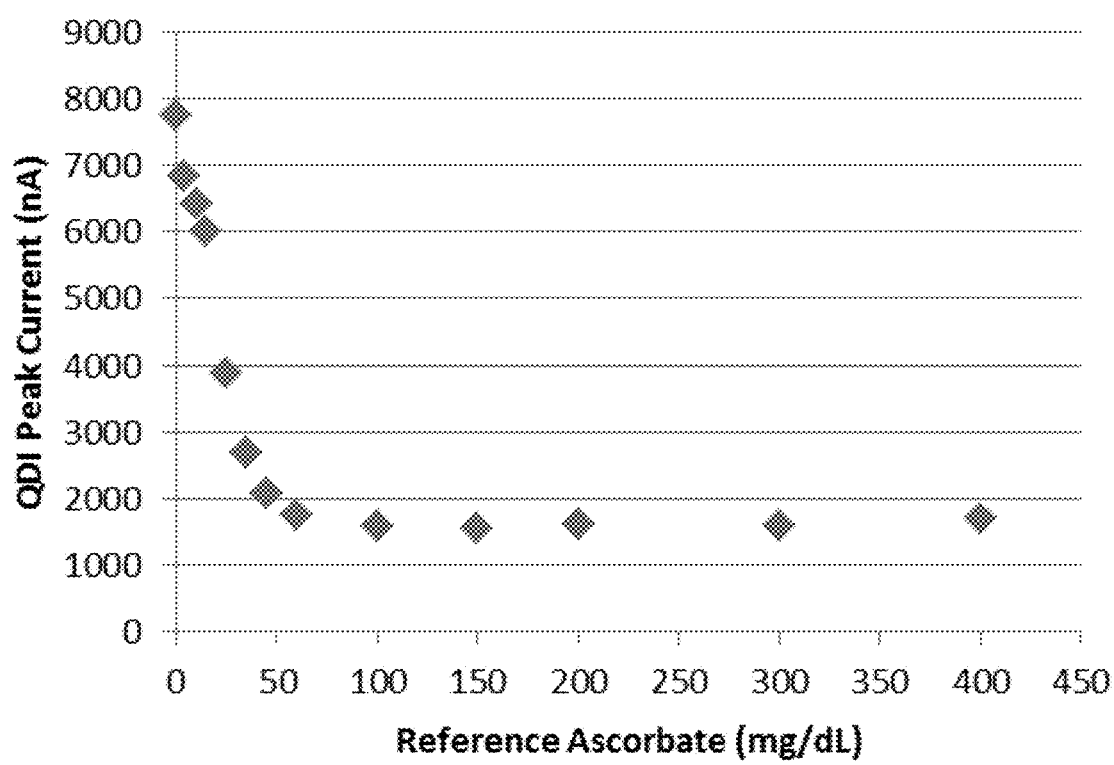
FIG. 10 is a graph of QDI peak current in nA vs. reference ascorbate in mg/dL.
Figure 11:
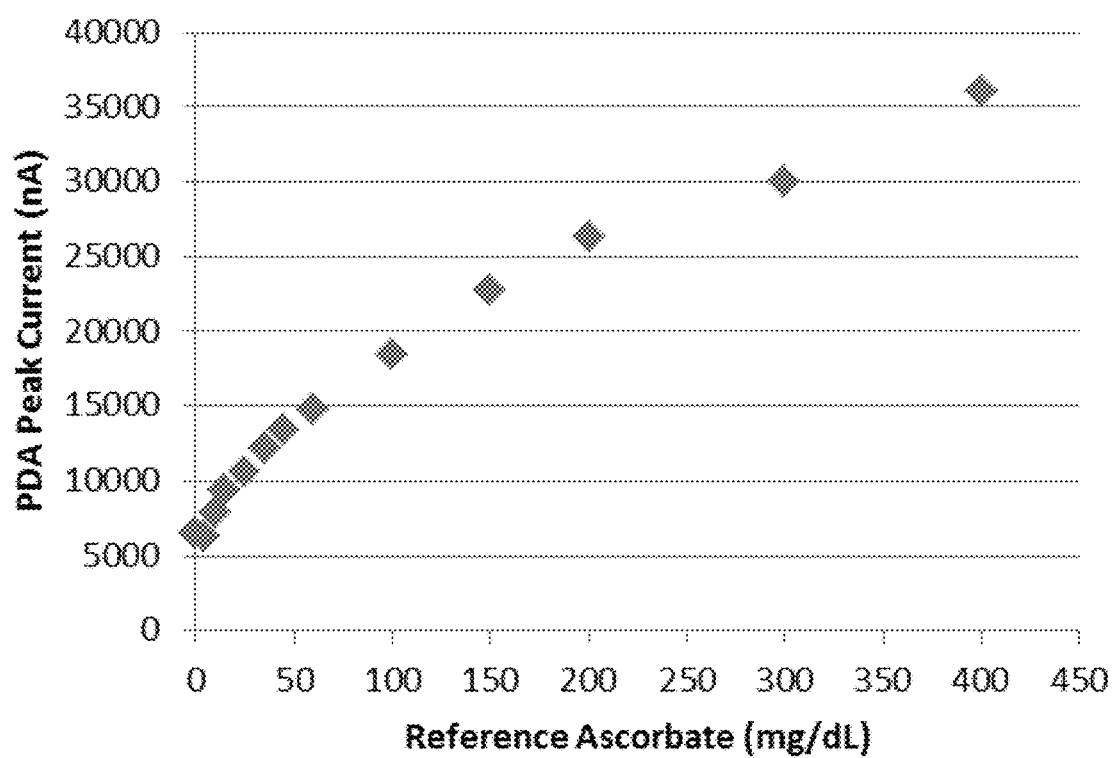
FIG. 11 is a graph of PDA peak current in nA vs. reference ascorbate in mg/dL.

FIGS. 10-11 show a more detailed view of the data illustrated in FIG. 9 with respect to the QDI and PDA features, respectively. Specifically, FIG. 10 shows a clear decrease in the peak current corresponding to QDI as the ascorbate level increases. In contrast, FIG. 11 shows a clear increase in the peak current corresponding to PDA as the ascorbate level increases. If the amount of PDA is assumed to be directly proportional to glucose, it is possible to understand how the presence of high ascorbate levels would cause an erroneous, elevated glucose reading. These and similar QDI and/or PDA features may be utilized in a variety of antioxidant failsafes and/or chemistry health failsafes, examples of which will now be described.

One exemplary method includes constructing an antioxidant failsafe that does not require a quantitative estimate of the antioxidant. For example, a group of representative training data can be divided into two classes, one containing ascorbate levels ≤10 mg/dL, and another containing ascorbate levels >10 mg/dL. It has been shown that an ascorbate level of 10 mg/dL produces a biased glucose estimate that is still within Zones A and B of the Parkes Error Grid, thereby resulting in a glucose prediction error that would not lead an individual to respond improperly, such as delivering insulin when it is not really needed. The training set can then be used with any number of mathematical methods for classification. Classification methods provide way to classify a new, or unknown, observation based upon a set of known classes. These exemplary classifications are based upon the ability to accurately discriminate between classes rather than predict actual ascorbate value. In this case, any ascorbate levels ≤10 mg/dL belong to only one class; likewise, any ascorbate levels >10 mg/dL belong only to the other class. To implement a failsafe, it is only necessary to accurately determine the class to which a new observation belongs.

The data used to train and implement the classifier determined can be from current response information of DC Block 2. Alternatively, analogous failsafes may be created using the PDA-related current response information of DC Block 1 and additional AC information, although it should be realized that many unrelated factors can influence the current response. Thus, an antioxidant classifier based upon DC Block 1 would be based upon an assumption that the increased current caused by, for example, ascorbate can always be distinguished from increased current due to other factors—even for new, non-conforming sample types that are yet unknown and may not have been considered in training the classifier. In contrast, DC Block 2 provides new information about QDI, thereby providing a way to directly determine the presence of an antioxidant such as ascorbate.

Returning to FIG. 1 and its associated discussion, it is important to understand that this type of antioxidant failsafe is made possible because of the particular choice of NA as a redox mediator. However, any redox mediator that forms a species that can be easily reduced by an antioxidant such as ascorbate could be used in a similar manner to implement the approaches described herein, provided that electrooxidation of the additional amount of redox mediator reduced by the antioxidant produces a response effect that is evident at potential excitations during DC Block 2, where the analyte-based electrooxidation of reduced redox mediator is not typically evident. This is not the case with some of the common redox mediators used for SMBG, but is particularly one effect of a redox mediator system based on NA.

In addition to ascorbate, it is believed that any interferent can be monitored that readily produces essentially a unique, but similar, signature (e.g., a decrease in the QDI feature, an increase in the QDI feature, a decrease in the PDA feature or an increase in the PDA feature). Even a lack of specificity among multiple interferents would not negate any of the advantages described above. If the FAD-GDH chemistry with NA-derived redox mediator is working properly, a sample (at given glucose, Hct and temperature levels) should produce a current response with a characteristic ratio of the QDI and PDA peak currents.

Reagent Layer/Chemistry Health Failsafes and Measurement Methods: In addition to the antioxidant failsafe methods described above, hydrated reagent layer failsafe methods are provided. The methods generally begin as above by applying a test sequence having at least one DC block, and alternatively at least one AC block and even a second DC block.

If the hydrated chemistry system (meaning the reagent system combined with a fluidic sample such as blood) and the redox mediator are working properly, any normal sample (at given analyte such as glucose, hematocrit and temperature levels) will produce a current response with a QDI feature and a characteristic ratio of the QDI and PDA peak currents ($M_{ox}$:$M_{red}$). If the QDI feature is not discernible, this implies that there is something seriously wrong with the reagent layer system. This situation will result in the production of additional current arising from a different mechanism than just the reaction with the analyte, thereby leading to an incorrect, dangerous reading. Therefore, checking for the simple qualitative existence or absence of the QDI feature provides the basis for the reagent layer health failsafe. This check can be performed mathematically in a variety of ways, including pattern recognition, discriminant analysis and simple heuristic comparisons using selected values from the current response.

In contrast to the methods above, which utilize quantitative prediction of antioxidant, these methods utilizes antioxidant discrimination, enabled by a numerical classification method. Like the antioxidant failsafe methods described above, the chemistry health failsafe methods are based upon response information from DC Block 2 (thereby extending test time); however, the use of SRBPs offers a distinct advantage, namely the ability to see the QDI feature. Antioxidants such as ascorbate react directly with QDI, thereby reducing the intensity of the feature, enabling: (1) the ability to detect ascorbate directly; and (2) the ability to clearly distinguish increases in PDA due to ascorbate versus other numerous other factors. The ability to detect a ratio of the PDA and QDI features also provides the basis for a reagent layer health failsafe, which can be used to determine whether the biosensor chemistry and redox mediator are working properly. These new capabilities are made possible by the new information contained only in Block 2.

The reagent layer failsafe can be demonstrated using a classifier, or discriminator, that distinguishes samples with ≤10 mg/dL ascorbate from samples containing >10 mg/dL ascorbate. The classifier can be constructed according to the following equation:

$$\text{Probability}(\text{Ascorbate} > T1) = \frac{\sum_{i=1}^{M} \alpha_i \cdot \tanh\left(\sum_{j=1}^{N} \beta_j \cdot O_j\right)}{1 + \sum_{i=1}^{M} \alpha_i \cdot \tanh\left(\sum_{j=1}^{N} \beta_j \cdot O_j\right)}.$$

In the above equation $\beta_j$ are optimized coefficients for $O_j$ values selected from the AC Block and DC Block 2.

To generate the results shown below, 35 values (N=35) were chosen using an optimal variables selection procedure, which consisted of eight (8) AC values (phase and admittance at four different frequencies) and twenty-nine (29) values from the Block 2 DC current response. The selection of Block 2 DC current response values was intentionally limited to the first negative- and positive-going potential ramps, and interestingly, almost all of the selected DC variables corresponded to the QDI feature on the positive-going ramp.

The failsafe described by the above equation is activated if Probability (Ascorbate>T1) is greater than T2, where T2 is in the interval [0, 1]. The result of the nonlinear function indicates the probability that a new sample belongs to one of the two classes. As shown in Table 7, a training set was constructed using samples representing a wide range of glucose, hematocrit, temperature and humidity levels, various storage conditions, clinical interferences and ascorbate levels. The training set contained 24,982 samples with ascorbate levels ≤10 mg/dL and 1145 samples with ascorbate>10 mg/dL. After training, only three (3) observations from each class were misclassified, corresponding to a classification accuracy of 99.99% and 99.74% for each class, respectively. These results are summarized in Table 7.

TABLE 7

Training set composition and performance.

| Training Set | Predicted Ascorbate ≤10 mg/dL | Predicted Ascorbate >10 mg/dL | All |
|---|---|---|---|
| Actual Ascorbate ≤10 mg/dL | 24979 | 3 | 24982 |
| Actual Ascorbate >10 mg/dL | 3 | 1142 | 1145 |
| All | 24982 | 1145 | 26127 |

The new classifier also was tested using a test data set, which did not contain any of the same samples used in training. Like the training set, the independent test set contained samples representing a wide range of glucose, hematocrit, temperature and humidity levels, various storage conditions, clinical interferences and ascorbate levels. The test set contained training set contained 12,492 samples with ascorbate levels ≤10 mg/dL and 575 samples with ascorbate>10 mg/dL. Application of the classifier resulted in the misclassification of 11 observations in the ≤10 mg/dL class and 3 observations in the >10 mg/dL class, corresponding to an overall classification accuracy of 99.91% and 99.48% for each class, respectively. These results are summarized in Table 8.

TABLE 8

Independent test set composition and performance.

| Independent Test Set | Predicted Ascorbate ≤10 mg/dL | Predicted Ascorbate >10 mg/dL | All |
|---|---|---|---|
| Actual Ascorbate ≤10 mg/dL | 12481 | 11 | 12492 |
| Actual Ascorbate >10 mg/dL | 3 | 572 | 575 |
| All | 12494 | 583 | 13067 |

These represent only exemplary results, as no attempts were made to further study the effects of picking different DC Block 2 values or to further optimize the composition of samples comprising the training set. These certainly illustrate that very good classification results can be obtained, thereby providing a basis for an ascorbate failsafe.

This ascorbate failsafe was demonstrated using DC current response values from the first negative- and positive-going ramps in DC Block 2, thereby illustrating that the total test sequence can be much shorter by truncating DC Block 2. However, the ascorbate classifier could also have been constructed from a later slow-ramped, bi-polar cycle comprising the DC Block 2 applied potential. The reagent layer health failsafe methods require at least one SRBP cycle of the applied potential, but does not require additional cycles having the same or different ramp rates. Furthermore the one or more SRBP cycle(s) can occur before or immediately after DC Block 1. The ascorbate failsafe will still work in the same manner.

The methods described above are exemplary and non-limiting. Additional classes could be added, indicating ascorbate values in a range where a reliable correction could be made. This could be accomplished by combining both exemplary methods described herein. In this case, a quantitative prediction of the true ascorbate level could be made for samples within the range, and this value could be used to correct the glucose value delivered by the meter. The above method is also not intended to limit the type of classification method that could be employed. Other methods, such as decision trees, K-nearest neighbors (KNN), neural networks, etc. could also be used to construct a classifier.

The reagent layer health failsafe therefore involves simply checking for the existence of the QDI feature. If the chemistry and mediator onboard the biosensor is working as expected, a QDI feature should exist and should exhibit a defined range of ratios with the PDA feature. If the QDI feature is not discernable, this implies that there is something wrong with the reagent layer. This situation will result in the production of additional current arising from a different mechanism than just the reaction with glucose, thereby leading to an incorrect glucose reading. The check for the existence of the QDI peak can be performed mathematically in a variety of ways, including pattern recognition, discriminant analysis, and simple heuristic comparisons using selected values from the current response.

A practical example of how both exemplary methods could be implemented by an SMBG system may be described by the following operations:

(1). after DC Block 1, apply DC Block 2 and determine whether the expected QDI feature is present. If not, then stop the test and send an error code (Chemistry health failsafe).

(2). using current response data from DC Block 1, use the ascorbate classifier to predict the class membership of the new sample (ascorbate failsafe); wherein:

(a). if the sample is classified as having ≤10 mg/dL ascorbate, then report a glucose value;

(b). if the sample is classified as having >10 mg/dL ascorbate, then report an error code;

(c). (optional) if the sample is classified into an optional third class, indicating that correction of the glucose value is possible and reliable, then predict the ascorbate level and report a compensated (corrected) glucose value; or (d). avoid (or simply obviate the need for) application of DC Block 2.

It should be understood that this logical flow of operations is presented as an example and is not limiting.

The methods can be used with amperometric SMBG systems that utilize at least one DC test sequence in which the applied voltage is ramped at a rate that makes it possible to distinguish the QDI and PDA electrochemical signature(s) associated with the mediator. The ramped voltage may be linear or follow other functional forms, such as a sine or cosine wave. The methods are applicable to any electrochemical system containing a mediator that is reduced by ascorbate and which has a unique voltage-current signature that differs from that of the enzyme. It should also be noted that that ascorbate and glucose can both be predicted from AC information and DC Block 2 alone, thereby eliminating the need for DC Block 1. Furthermore, the aspects of the methods could be exercised as described, regardless of what information is used to predict glucose. The DC Block 1 current response used to quantify glucose is proportional to the amount of PDA. Since DC Block 2 contains signatures for both QDI and PDA, it is possible to quantify glucose based upon the intensity of the PDA feature, and simultaneously, it is possible to quantify ascorbate based upon the QDI and/or the ratio of the QDI and PDA features. The methods also are applicable to coulometric-based SMBG systems, assuming they employ a chemistry system and mediator that permits analogous detection of ascorbate using a similar potential sequence with slow-ramped, bi-polar excitation.

It shall be understood that the probabilistic classifier may be substantially the same or identical for techniques based upon DC Block 1 or DC Block 2. It shall be further understood that the quality of the classifier in terms of prediction performance for both the training and prediction sets was very high and that the training and prediction sets were assembled using a very wide variety of data representing many different levels of glucose, temperature, Hct, salt, interferences, and other variables. All of the various techniques disclosed herein show excellent performance.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

The invention claimed is:

1. A method of failsafing an electrochemical measurement of an analyte from antioxidant interference, the method of comprising the steps of:
    applying an electrical test sequence to an electrochemical biosensor, the biosensor comprising:
    an electrode system,
    a reagent including a redox mediator in electrical communication with the electrode system, and
    a receptacle configured to contact the fluid sample provided to the biosensor,
with a fluid sample in fluidic contact with the reagent, wherein the test sequence comprises at least one direct current (DC) block, wherein the at least one DC block includes a pulsed sequence alternating between at least one excitation potential and at least one recovery potential, and wherein a closed circuit condition of the electrode system is maintained during the at least one recovery potential;
    measuring current response information to the test sequence, including information from the at least one excitation potential and the at least one recovery potential;
    determining an analyte concentration of the fluid sample utilizing the information of the excitation current response and the recovery current response, the determining compensating for at least one interferent; and
    providing a statistical antioxidant failsafe using either a classifier or a discriminator to determine whether an antioxidant is interfering with the analyte concentration, wherein the statistical antioxidant failsafe is based upon information from the at least one DC block that relates to the redox mediator.

2. The method of claim 1, wherein the antioxidant determination is utilized to provide at least 10/10 performance.

3. The method of claim 1, wherein the antioxidant determination is at least in part to reject an analyte concentration measurement or determination.

4. The method of claim 1, wherein the antioxidant determination is at least in part to correct an analyte measurement or determination.

5. The method of claim 1, where the failsafe is activated if the antioxidant level is determined to be greater than 10 mg/dL.

6. A method of failsafing an electrochemical measurement of an analyte in a fluid sample, the method comprising the steps of:
    applying an electrical test sequence to an electrochemical biosensor, the biosensor comprising:
    an electrode system,
    a reagent including a redox mediator in electrical communication with the electrode system, and
    a receptacle configured to contact the fluid sample provided to the biosensor,
with the fluid sample in fluidic contact with the reagent, wherein the test sequence comprises at least one direct current (DC) block, wherein the at least one DC block is a slow-ramped bi-polar potential (SRBP) that alternates between about −450 mV to about +450 mV at two different ramp rates, and wherein a closed circuit condition of the electrode system is maintained during the DC block;
    measuring the information from the response to the test sequence; and
    providing a reagent layer health failsafe based upon a ratio of an oxidized form of a redox mediator ($M_{ox}$) to a reduced form of the redox mediator ($M_{red}$), wherein the failsafe prevents reporting of an analyte concentration if $M_{red}$ is above a predetermined level.

7. The method of claim 6, wherein the failsafe is activated when there is a lack of an expected $M_{ox}$ feature, wherein the expected $M_{ox}$ feature is selected from the group consisting of a duration, a shape and/or a magnitude of a current response based upon an amount of $M_{ox}$.

8. The method of claim 6, wherein the test sequence further comprises at least one alternating current (AC) block.

9. The method of claim 6, wherein the test sequence further comprises a second DC block.

* * * * *